United States Patent
Poetsch et al.

(10) Patent No.: US 6,200,654 B1
(45) Date of Patent: *Mar. 13, 2001

(54) 1,4-DISUBSTITUTED 2,6-DIFLUOROBENZENE COMPOUNDS, AND A LIQUID-CRYSTALLINE MEDIUM

(75) Inventors: Eike Poetsch, Mühltal; Volker Meyer, Gross-Zimmern; Volker Reiffenrath, Rossdorf; Andreas Wachtler, Griesheim; Ulrich Finkenzeller, Plankstadt; Hans Adolf Kurmeier, Seeheim-Jugenheim; Reinhard Hittich, Modautal, all of (DE); Bernhard Rieger, Yokohama (JP); David Coates, Wimborne (GB); Simon Greenfield; Robert William Clemitson, both of Poole (GB)

(73) Assignee: Merck Patent Gesellschaft mit beschrankter Haftung (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/917,167

(22) Filed: Aug. 25, 1997

Related U.S. Application Data

(60) Continuation of application No. 08/449,559, filed on May 24, 1995, now abandoned, which is a division of application No. 08/402,555, filed on Mar. 13, 1995, now abandoned, which is a continuation of application No. 07/659,320, filed on Feb. 22, 1991, now abandoned.

(30) Foreign Application Priority Data

| Dec. 6, 1989 | (DE) | P 39 40 343 |
| Dec. 19, 1989 | (DE) | P 39 41 881 |
| Jan. 10, 1990 | (DE) | P 40 00 535 |
| Jan. 10, 1990 | (DE) | P 40 00 534 |
| Dec. 6, 1990 | (EP) | PCT/EP90/02109 |

(51) Int. Cl.[7] .................. C09K 19/20; C09K 19/12; C09K 19/34; C09K 19/30; C07C 25/13
(52) U.S. Cl. ............... 428/1.1; 252/299.61; 252/299.62; 252/299.63; 252/299.64; 252/299.65; 252/299.66; 252/299.67; 570/127; 570/129; 570/131
(58) Field of Search ............ 252/299.01, 299.61, 252/299.63, 299.62, 299.66, 299.67; 570/127, 129, 131, 182; 428/1.1

(56) References Cited

U.S. PATENT DOCUMENTS 4,419,264  12/1983  Eidenschink et al. .

(List continued on next page.)

FOREIGN PATENT DOCUMENTS 064 193   4/1982   (EP) .
317 175  11/1988   (EP) .
387 032   3/1990   (EP) .

OTHER PUBLICATIONS

Chemical Abstracts, Band 107, No. 20, Nov. 16, 1987. P. 793.
Chemical Abstracts, Band 110, No. 14, Apr. 3, 1989, p. 360.
Molecular Crystals and Liquid Crystals, Band 172, Jul. 1988, (Chur, CH) G.W. Gray et al., pp. 165–189.

*Primary Examiner*—Shean C. Wu
(74) *Attorney, Agent, or Firm*—Millen, White, Zelano & Branigan, P.C.

(57) ABSTRACT

1,4-disubstituted 2,6-difluorobenzene compound of formula I

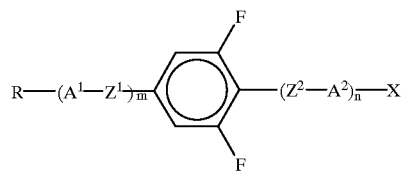

wherein
R is an alkyl or alkenyl radical,
$A^1$ and $A^2$, in each case independently of one another, are
(a) a trans-1,4-cyclohexylene radical in which a $CH_2$ group may be replaced by —O— and/or —S,
(b) a 1,4-phenylene radical in which a CH group may be replaced by N,
(c) 1,4-cyclohexenylene, 1,4-bicyclo(2,2,2)octylene, piperidine-1,4-diyl, naphthalene-2,6-diyl, decahydronaphthalene-2,6-diyl or 1,2,3,4-tetrahydronaphthalene-2,6-diyl,
$Z^1$ and $Z^2$ are —CO—O—, —O—CO—, —$CH_2$—O—, —O$CH_2$—, —$CH_2CH_2$—, —CH=CH—, —C≡C— or a single bond
m and n are 0, 1, 2 or 3,
(m+n) is 1, 2 or 3,
X is R or F, Cl, $CF_3$, —$OCF_3$, or —$OCHF_2$, —$OCF_5$, —CN or —NCS
with the proviso that at least one of the radicals $A^1$ and $A^2$ present in the molecule is

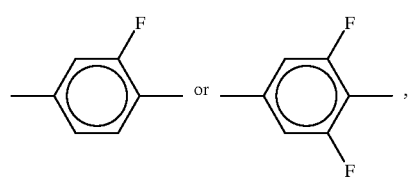

are suitable as components of liquid-crystalline media.

4 Claims, No Drawings

U.S. PATENT DOCUMENTS

| | | |
|---|---|---|
| 4,551,264 | 11/1985 | Eidenschink et al. . |
| 4,834,905 | 5/1989 | Eidenschink et al. . |
| 4,853,152 | 8/1989 | Goto . |
| 4,884,609 | 12/1989 | Yamada . |
| 4,970,022 | 11/1990 | Scheuble et al. . |
| 5,032,313 | 7/1991 | Goto . |
| 5,032,814 | 7/1991 | Goto et al. . |
| 5,069,814 | 12/1991 | Suzuki et al. . |
| 5,273,680 | 12/1993 | Gray et al. . |
| 5,372,746 * | 12/1994 | Buchecker et al. ............. 252/299.61 |
| 5,582,767 * | 12/1996 | Buchecker et al. ............. 252/299.66 |
| 5,589,102 * | 12/1996 | Bartmann et al. ............... 252/299.01 |
| 5,714,088 * | 2/1998 | Miyazawa et al. ............. 252/299.63 |
| 5,716,543 * | 2/1998 | Schlosser et al. ............. 252/299.63 |
| 5,718,840 * | 2/1998 | Plach et al. ..................... 252/299.66 |
| 5,723,068 * | 3/1998 | Hachiya et al. ................ 252/299.63 |
| 5,725,799 * | 3/1998 | Bremer et al. .................. 252/299.67 |
| 5,730,904 * | 3/1998 | Bartmann et al. ............. 252/299.63 |
| 5,753,142 * | 5/1998 | Plach et al. ...................... 252/299.6 |
| 5,755,994 * | 5/1998 | Kondo et al. ................... 252/299.61 |
| 5,762,828 * | 6/1998 | Tanaka et al. .................. 252/299.63 |
| 5,855,814 * | 1/1999 | Matsui et al. ................... 252/299.67 |

\* cited by examiner

1,4-DISUBSTITUTED 2,6-DIFLUOROBENZENE COMPOUNDS, AND A LIQUID-CRYSTALLINE MEDIUM

This application is a continuation of application Ser. No. 08/449,559, filed May 24, 1995 now abandoned, which is divisional of application Ser. No. 08/402,555, filed Mar.13, 1995 abandoned, which is a continuation of Ser. No. 07/659,320, filed Feb. 22, 1991, now abandoned.

The invention relates to novel 1,4-disubstituted 2,6-difluorobenzene compounds of the formula I

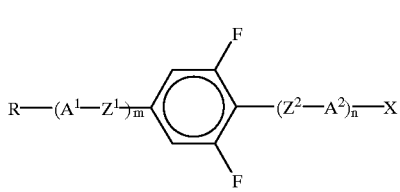

where
R is an alkyl or alkenyl radical having 1 to 15 carbon atoms which is unsubstituted or at least monosubstituted by halogen, it also being possible for one or more $CH_2$ groups in these radicals to be replaced, in each case independently of one another, by —O—, —S—,

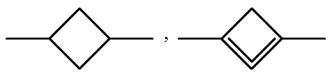

—CO—, —CO—O—, —O—CO— or —O—CO—O— in such a manner that oxygen atoms are not linked directly to one another, $A^1$ and $A^2$, in each case independently of one another, are
(a) a trans-1,4-cyclohexylene radical in which, in addition, one or more non-adjacent $CH_2$ groups may be replaced by —O— and/or —S—,
(b) a 1,4-phenylene radical in which, in addition, one or two CH groups may be replaced by N,
(c) a radical from the group comprising 1,4-cyclohexenylene, 1,4-bicyclo(2,2,2)octylene, piperidine -1,4-diyl, naphthalene-2,6-diyl, decahydronaphthalene -2,6-diyl and 1,2,3,4-tetrahydronaphthalene -2,6-diyl, it being possible for the radicals (a) and (b) to be substituted by CN or monosubstituted or disubstituted by fluorine, $Z^1$ and $Z^2$ in each case independently of one another, are —CO—O—, —O—CO—, —$CH_2$O—, —O$CH_2$—, —$CH_2CH_2$—, —CH=CH—, —C≡C— or a single bond,
m and n in each case independently of one another, are 0, 1, 2 or 3, where
(m+n) is 1, 2 or 3, and
X has one of the meanings of R or is F, Cl, —$CF_3$, —$OCF_3$—, —$OCF_2H$, —$OC_2F_5$, —CN or —NCS,
with the proviso that at least one of the radicals $Z^1$ and $Z^2$ present in the molecule is —CO—O—, —O—CO—, —$CH_2$—O—, —O$CH_2$—, —$CH_2CH_2$—, —CH=CH— or —C≡C and/or at least one of the radicals $A^1$ and $A^2$ present in the molecule is

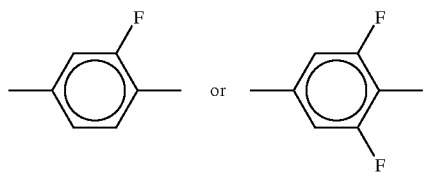

and/or n is 1 or 2,
where, in the case where —$(Z^2—A^2)_n$=

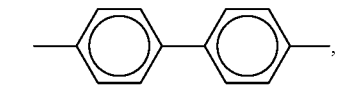

X is F, Cl, —$CF_3$, —$OCF_3$, —$OCF_2H$, —$OC_2F_5$, —CN or —NCS.

The invention furthermore relates to the use of these compounds as components of liquid-crystalline media, and to liquid-crystal and electrooptical displays which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel stable liquid-crystalline or mesogenic compounds which are suitable as components of liquid-crystalline media and in particular have at the same time comparatively low viscosity and a relatively high dielectric anisotropy.

It has now been found that compounds of the formula I are eminently suitable as components of liquid-crystalline media. In particular, they have comparatively low viscosities. Using them, stable liquid-crystalline media which have a broad mesophase range, advantageous values for the optical and dielectric anisotropy and outstanding ultraviolet and temperature stability are obtained.

Liquid crystals of the formula

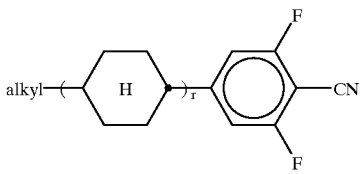

r = 1 or 2 have already been disclosed in DE 3209178. JP 62-103057 discloses compounds of the formulae

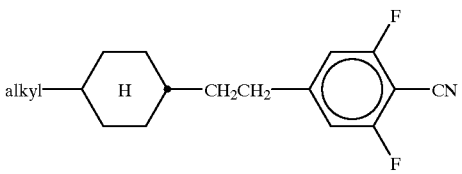

and

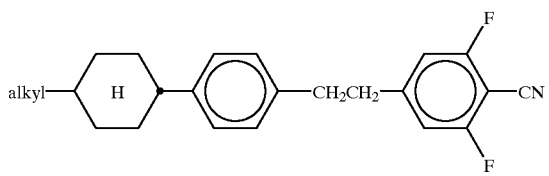

Finally, JP 63-216858 describes compounds of the formula

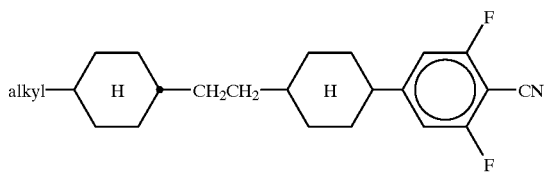

In view of the very wide range of areas of application of such compounds having very high $\Delta\epsilon$, it was, however, desirable to have further compounds available which have properties precisely customized to the particular applications.

Liquid crystals of the formula

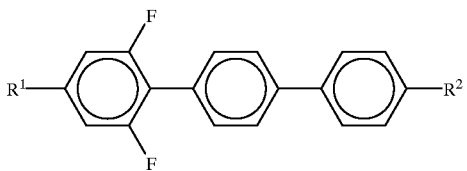

have already been disclosed in WO 89/02425 and are distinguished by high birefringence and relatively high viscosity.

In view of the very wide variety of areas of application of such compounds having positive $\Delta\epsilon$, it was desirable to have further compounds available which have properties precisely customized to the particular applications.

In addition, the provision of the compounds of the formula I very generally considerably extends the range of liquid-crystalline substances which are suitable, from various applicational points of view, for the preparation of liquid-crystalline mixtures.

The compounds of the formula I have a broad field of application. Depending on the choice of substituents, these compounds can be used as base materials from which liquid-crystalline media are predominantly composed; however, compounds of the formula I can also be added to liquid-crystalline base materials from other classes of compound, in order, for example, to influence the dielectric and/or optical anisotropy of a dielectric of this type and/or to optimize its threshold voltage and/or its viscosity.

In the pure state, the compounds of the formula I are colorless and form liquid-crystalline mesophases in a very favorable temperature range for electrooptical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electrooptical display elements, which contain media of this type.

For reasons of simplicity below, $A^3$ is a radical of the formula

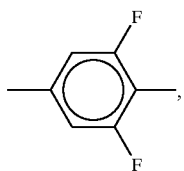

Cyc is a 1,4-cyclohexylene radical, $A^4$ is a radical of the formula

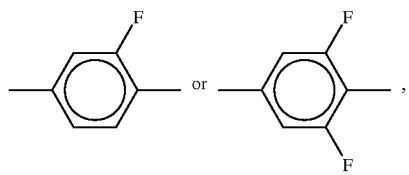

Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical.

The compounds of the formula I accordingly include the preferred dinuclear compounds of the subformulae Ia and Ib:

Ia

Ib

Trinuclear compounds of the sub-formulae Ic to If:

Ic

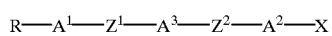

Id

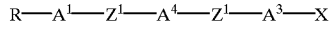

Ie

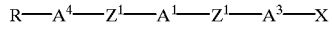

If and tetranuclear compounds of the sub-formulae Ig to Ij:

Ig

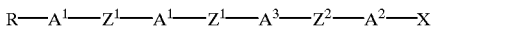

Ih

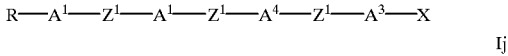

Ii

Ij

Of these, those of the sub-formulae Id, Ie, Ih and Ii are particularly preferred.

In the compounds of the formulae above and below, X is preferably —OCF$_3$, —OCHF$_2$, —CF$_3$, F or Cl. Likewise preferred are compounds of the formulae above and below in which X has one of the meanings of R.

In the case where X is F, Cl, —CF$_3$, —OCF$_3$, —OCHF$_2$, —OC$_2$F$_5$, —CN or —NCS, at least one of the radicals $A^1$ and $A^2$ present in the molecule of the formula I is preferably

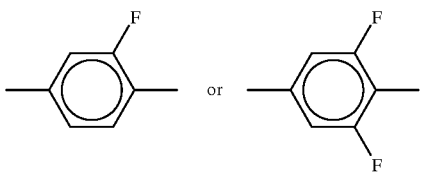

and/or n is 1 or 2.

R is preferably alkyl, furthermore alkoxy. $A^1$ and/or $A^2$ are preferably Phe, Cyc, Che, Pyr or Dio. The compounds of the formula I preferably contain not more than one of the radicals Bi, Pyd, Pyr, Dio or Dit.

Preferred compounds of the formula I and of all the sub-formulae are those in which $A^1$ and/or $A^2$ are 1,4-phenylene which is monosubstituted or disubstituted by F or monosubstituted by CN. These are, in particular, 2-fluoro-1,4-phenylene, 3-fluoro-1,4-phenylene and 2,3-difluoro-1,4-phenylene, and 2-cyano-1,4-phenylene and 3-cyano-1,4-phenylene.

$Z^1$ and $Z^2$ are preferably a single bond, —CO—O—, —O—CO— and —CH$_2$CH$_2$—, and secondarily preferably —CH$_2$— and —OCH$_2$—. Preferably, only one of the groups $Z^1$ and $Z^2$ present in the molecule is other than a single bond.

If R is an alkyl radical and/or an alkoxy radical, it may be straight-chain or branched. It is preferably straight-chain, has 2, 3, 4, 5, 6 or 7 C atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one CH$_2$ group has been replaced by —CH=CH—, it may be straight-chain or branched. It is preferably straight-chain and has 2 to 10 C atoms. It is accordingly particularly vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one CH$_2$ group has been replaced by —O— and one has been replaced by —C—, these are preferably adjacent. These thus contain an acyloxy group —CO—O— or an oxycarbonyl group —O—CO—. These are preferably straight-chain and have 2 to 6 C atoms. They are accordingly particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If R is an alkyl radical in which one CH$_2$ group has been replaced by unsubstituted or substituted —CH=CH— and an adjacent CH$_2$ group has been replaced by CO or C—O or O—CO—, it may be straight-chain or branched. It is preferably straight-chain and has 4 to 13 C atoms. It is accordingly particularly acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups R which are suitable for polymerization reactions are suitable for the preparation of liquid-crystalline polymers.

Compounds of the formula I containing branched wing groups may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy or 1-methylheptoxy.

If R is an alkyl radical in which two or more CH$_2$ groups have been replaced by —O— and/or —CO—O—, it may be straight-chain or branched. It is preferably branched and has 3 to 12 C atoms. It is accordingly particularly biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups R which are suitable for polycondensations are suitable for the preparation of liquid-crystalline polycondensates.

The formula I covers the racemates of these compounds and the optical antipodes, and mixtures thereof.

Of these compounds of the formula I and the subformulae, those are preferred in which at least one of the radicals present therein has one of the preferred meanings indicated.

In the compounds of the formula I, those stereoisomers in which the rings Cyc and piperidine are trans-1,4-disubstituted are preferred. Those of the abovementioned formulae which contain one or more groups Pyd, Pyr and/or Dio in each case include the two 2,5-positional isomers.

The 1,4-cyclohexenylene group preferably has the following structures:

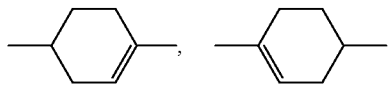

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart, Vol. IX, pp. 867 ff.), to be precise under reaction conditions which are known and suitable for the reactions mentioned. Use can also be made here of variants which are known per se, but are not described in greater detail here.

The compounds according to the invention can be prepared, for example, by reacting a compound of the formula II

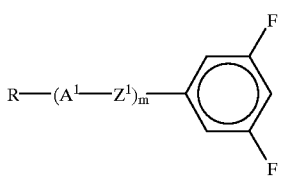

II in which R, $A^1$, $Z^1$ and m are as defined, in accordance with the following reaction schemes:

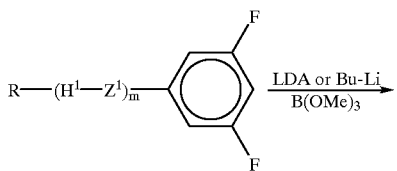

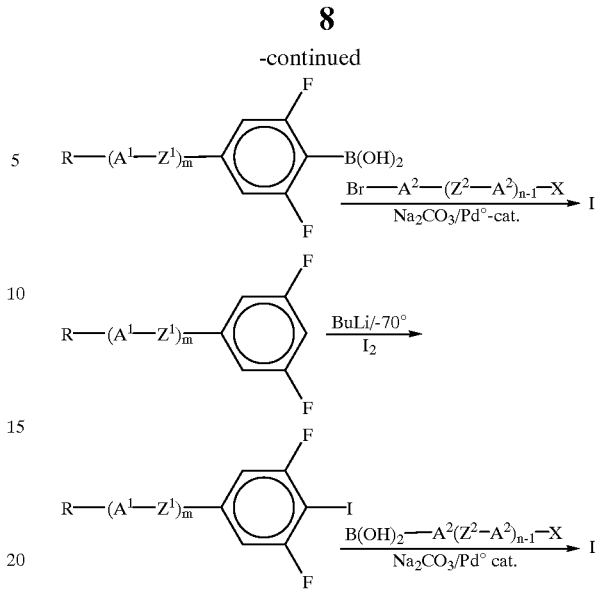

Further synthesis methods are apparent to a person skilled in the art. For example, appropriately 5-substituted 1,3-difluorobenzene compounds can be converted in accordance with the above scheme into 2-substituted 1,3-difluoro compounds, and the radical R—$(A^1—Z^1)_m$— can subsequently be introduced by customary reactions of liquid-crystal chemistry (for example esterification, etherification or coupling, for example in accordance with the article E. Poetsch, Kontakte (Darmstadt) 1988 (2), p. 15), or vice versa.

The compounds of the formula II can be prepared, for example, in accordance with the following synthetic schemes:

Scheme 1

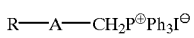

$(A = —(A^1—Z^1)_{m-1}-A^1—)$

R—A—$CH_2P^{\oplus}Ph_3I^{\ominus}$

Scheme 1

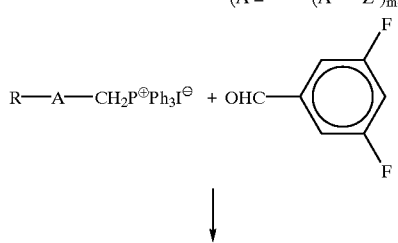

$(A = —(A^1—Z^1)_{m-1}-A^1—)$

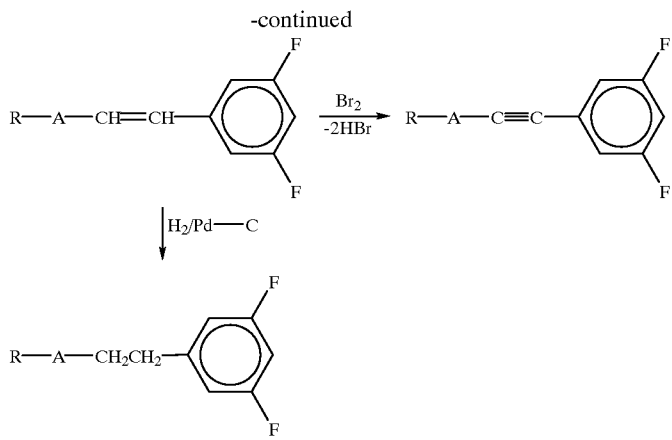
Scheme 2
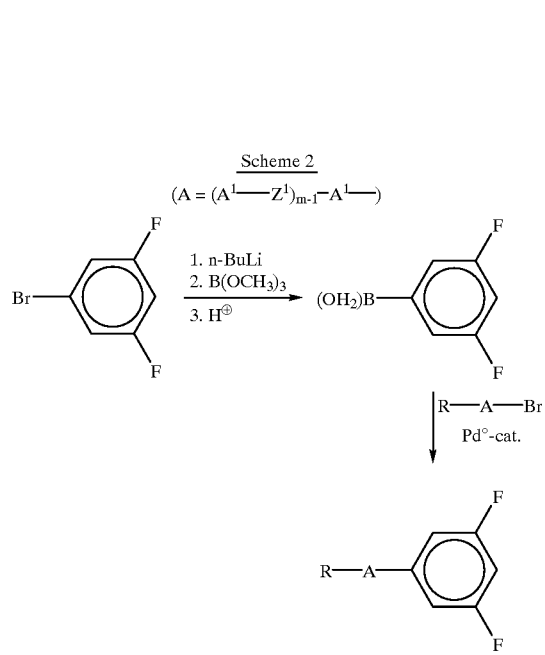
Scheme 3
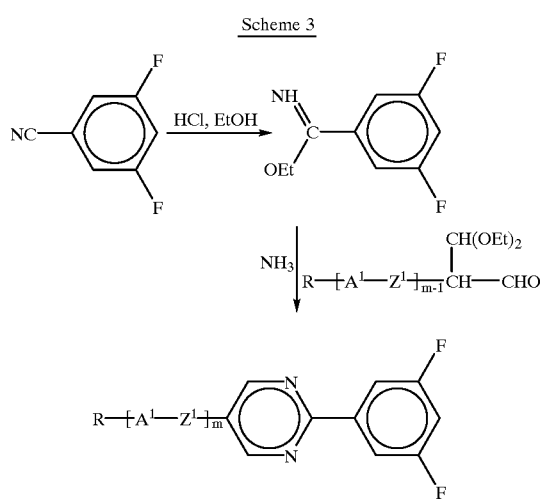
Scheme 4
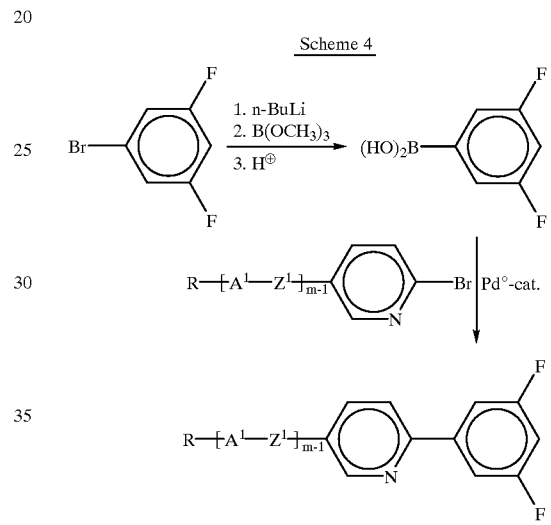
Scheme 5
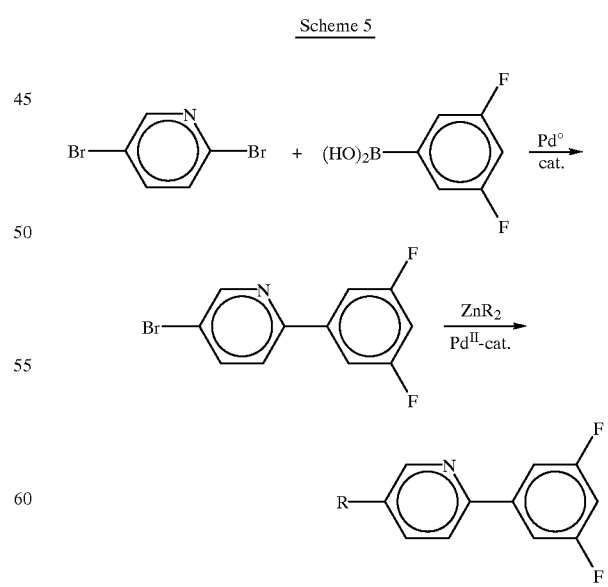
The starting materials are either known or can be prepared analogously to known compounds.

Esters of the formula I can also be obtained by esterification of appropriate carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes or alternatively by reacting metallated II with suitable electrophiles ($B(OH)_3/H_2O_2$ or $CO_2$).

The synthesis of some particularly preferred compounds is given in greater detail below (Y=H or F, Z=H or F):

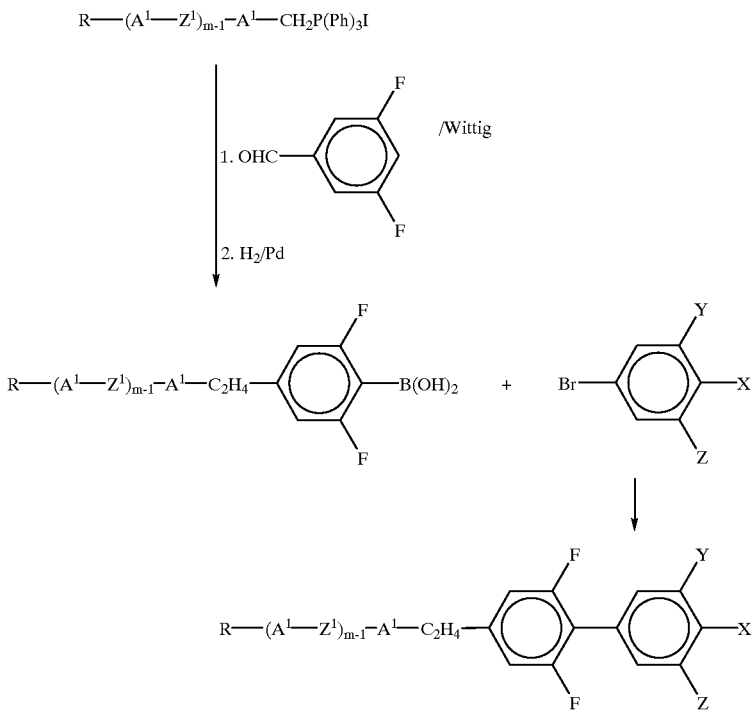

Scheme 6

In a further process for the preparation of the compounds of the formula I, an aryl halide is reacted with an olefin in the presence of a tertiary amine and a palladium catalyst (cf. R. F. Heck, Acc. Chem. Res. 12 (1979) 146). Suitable aryl halides are, for example, chlorides, bromides and iodides, in particular bromides and iodides. The tertiary amines which are necessary for the success of the coupling reaction, such as, for example, triethylamine, are also suitable as solvents.

Suitable palladium catalysts are, for example, salts thereof, in particular Pd(II) acetate, with organic phosphorus (III) compounds, such as, for example, triarylphosphines. The reaction can be carried out in the presence or absence of an inert solvent at temperatures between 0° and 150°, preferably between 20° and 100°; suitable solvents are, for example, nitriles, such as acetonitrile, or hydrocarbons, such as benzene or toluene. The aryl halides and olefins employed as starting materials are in many cases commercially available or can be prepared by processes known from the literature, for example by halogenation of appropriate parent compounds or by elimination reactions on appropriate alcohols or halides.

In this way, stilbene derivatives, for example, can be prepared. Stilbenes may also be prepared by reacting a 4-substituted benzaldehyde with an appropriate phosphorous ylide by the Wittig method. However, it is also possible to prepare tolans of the formula I by replacing the olefin by monosubstituted acetylene (Synthesis 627 (1980) or Tetrahedron Lett. 27, 1171 (1986)).

Furthermore, aryl halides can be reacted with aryl zinc compounds for the coupling of aromatics. These reactions are preferably carried out with addition of a catalyst, such as, for example, a palladium(0) complex, in inert solvents, such as hydrocarbons, at elevated temperatures, for example in boiling xylene, under a protecive gas.

Coupling reactions of alkynyl compounds with aryl halides may be carried out analogously to the process described by A. O. King, E. Negishi, F. J. Villani and A. Silveira in J. Org. Chem. 43, 358 (1978).

Tolans of the formula I can also be prepared by the Fritsch-Buttenberg-Wiechell rearrangement (Ann. 279, 319, 332, 1984), in which 1,1-diaryl-2-haloethylenes are rearranged in the presence of strong bases to give diarylacetylenes.

Tolans of the formula I can also be prepared by brominating the corresponding stilbenes and subsequently subjecting the bromination products to dehydrohalogenation. Use may be made here of variants of this reaction which are known per se but not described here in greater detail.

Ethers of the formula I are obtained by etherification of corresponding hydroxyl compounds, preferably corresponding phenols, the hydroxyl compound is expediently first converted into an appropriate metal derivative, for example into the corresponding metal alkali alcoholate or alkali metal phenolate by treatment with NaH, $NaNH_2$, NaOH, KOH, $Na_2CO_3$ or $K_2CO_3$. This can then be reacted with the appropriate alkyl halide, alkyl sulfonate or dialkyl sulfate, expediently in an inert solvent, such as, for example, acetone, 1,2-dimethoxyethane, DMF or dimethyl sulfoxide, or alternatively with an excess of aqueous or aqueous-alcoholic NaOH or KOH at temperatures between about 20° and 100°.

Particular preference is given to the compounds of the formula Ia

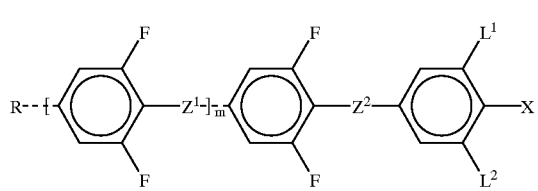

Ia in which R, $Z^1$, $Z^2$ and X are as defined above, m is 1 or 2, and $L^1$ and $L^2$, in each case independently of one another, are H or F. In the case where m=2, the two radicals $Z^1$ are identical or different. Preferably, at least one of the radicals $Z^1$ and $Z^2$ present in the molecule of formula Ia is other than a single bond and is preferably —$CH_2CH_2$—, —C≡C— or —CO—O—.

The compounds can be prepared by methods known per se starting from commercial

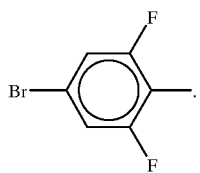

Apart from the linking possibilities shown in the above scheme, analogous synthesis processes by Friedel—Crafts acylation or the Wittig reaction with subsequent reduction or hydrogenation are possible for synthesizing the $CH_2$—$CH_2$ linked substances.

The

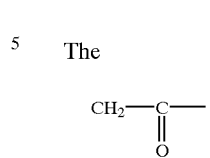

compounds can be converted into

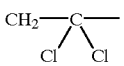

derivatives by chlorination using $PCl_5$ and subsequently into the acetylenes by HCl elimination using a base. The transformation of the —CH=CH— bridged substances, which can be prepared by Heck coupling or the Wittig reaction, is carried out in a conventional manner, for example by bromination and double elimination of HBr.

The carboxylate group is introduced analogously to the introduction of the $CH_2CH_2$ group (cf. compound 7, formula scheme below) by means of $CO_2$. The acids formed as intermediates can be esterified using the appropriate phenols, which can be prepared from 1 by synthesis step ba.

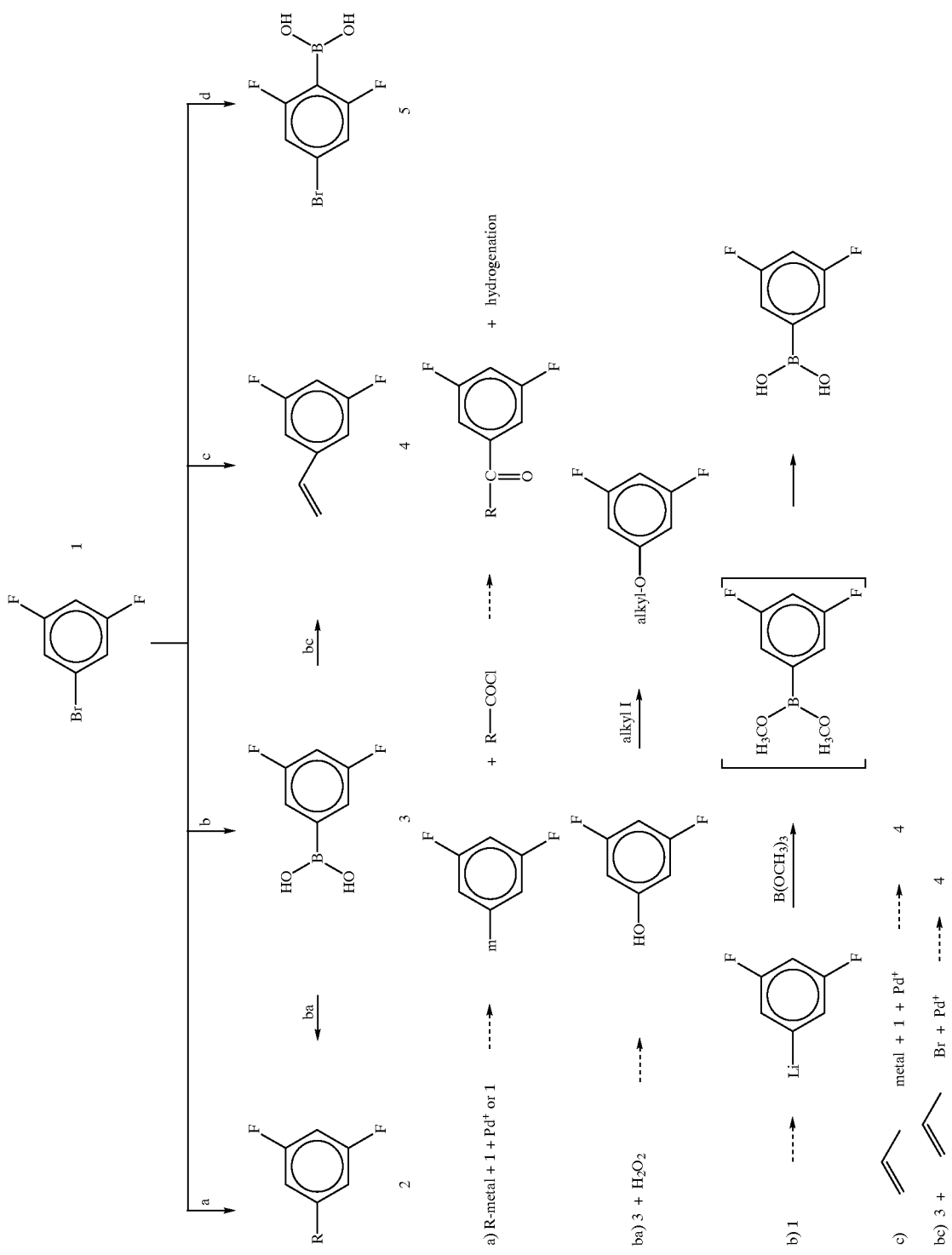

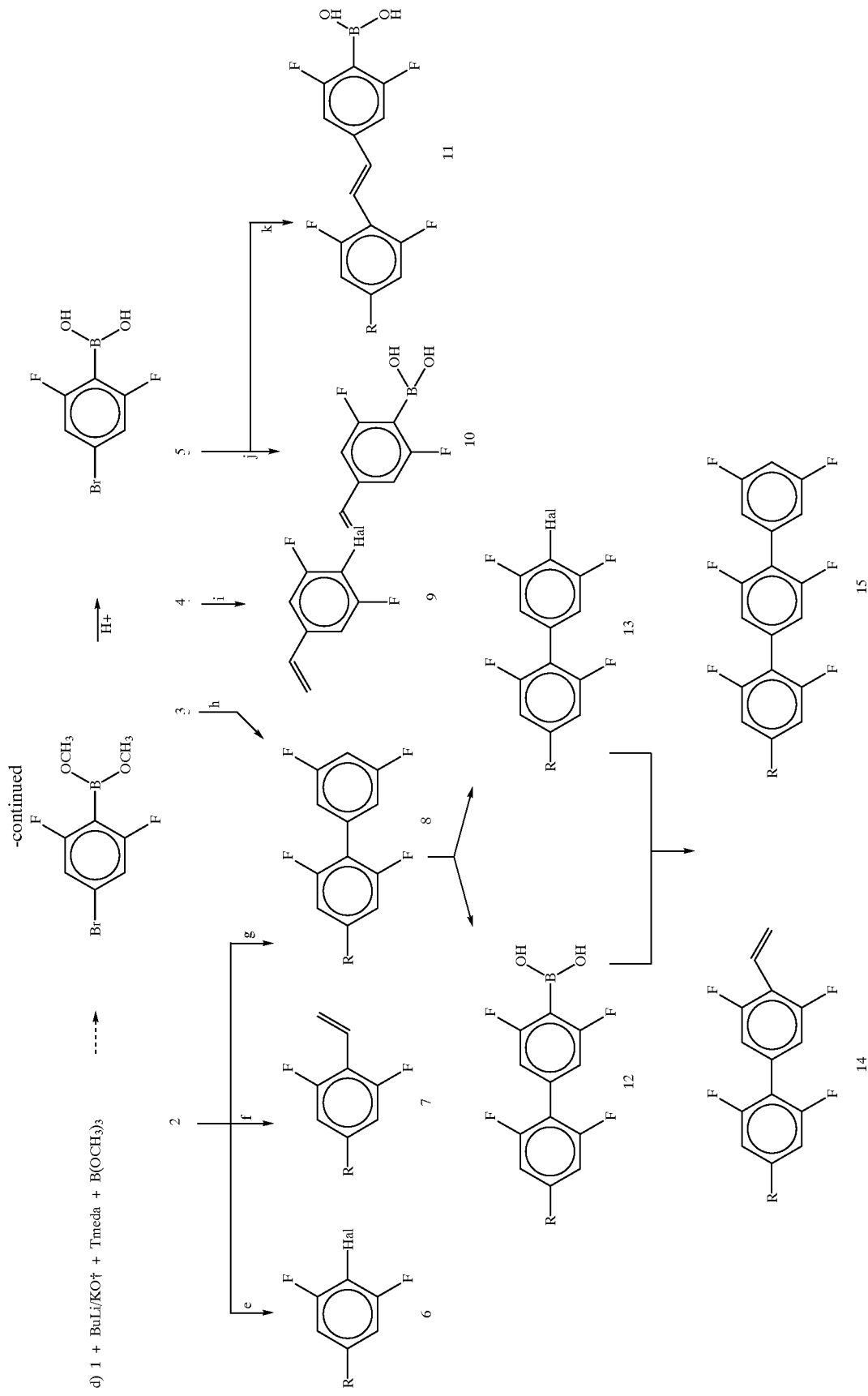

e) 2+BuLi/KOT+Tmeda+Hal$_2$ (Br$_2$ or I$_2$)
f) 2+BuLi/KOT+Tmeda+vinyl bromide+Pd$^O$
g) 2+BuLi/KOT+Tmeda+1 bromine, 3,5-difluorobendo+Pd$^O$
h) 6+3+pd$^O$
i) 4+BuLi/KOT+Tmeda+Hal$_2$ (Br$_2$ or I$_2$)
j) Dimethlyphenylvinylsilane+5+Pd$^O$\NBu$_4$F$^\ominus$+MeOH (Heck reaction)
k) 7+5+Pd$^O$ (Heck reaction)

Compound 8 can be converted into 12 in accordance with d) and into 13 analogously to e). 12 is converted into 14 by means of vinyl bromide in accordance with bc) and 13 is converted into 14 by means of divinyl zinc in accordance with c). 15 is obtained from 12 and 1 by cross-coupling in accordance with h) or from 13 and 3 by cross-coupling.

By a suitable combination of components 1–15, all the precursors of Ia in which Z is C≡C or a single bond can be synthesized. The CH=CH group can be converted into the CH$_2$—CH$_2$ or —C≡C— group.

The end group

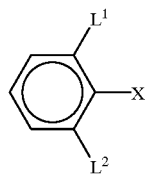

is introduced either using a coupling step with

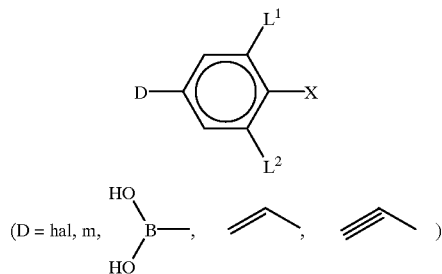

or by introducing X into compounds containing the end group

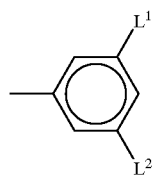

The preparation of likewise the compounds containing the CO$_2$ and/or C≡C bridging members can be carried out analogously in accordance with analogous formula schemes.

Further synthesis variants are known to those skilled in the art and proceed from appropriately substituted bromobiphenyls. Preferred variants are given in the following schemes. All the starting materials are either known or can be prepared analogously to known compounds.

These bromobiphenyls can be prepared in a manner known per se by cross-coupling reactions which are catalyzed by noble metals (E. Poetsch, Kontakte (Darmstadt) 1988 (2) p. 15).

One variant is given below as an example:

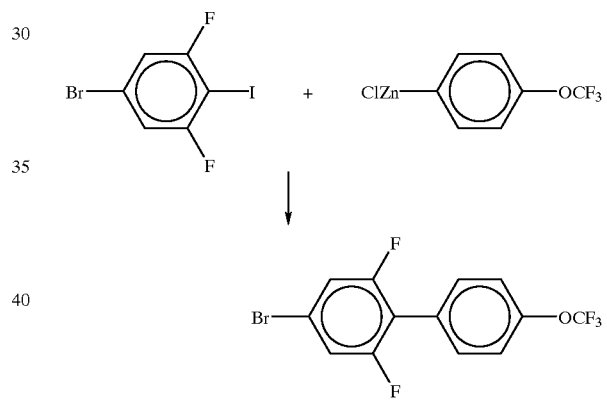

Scheme 3

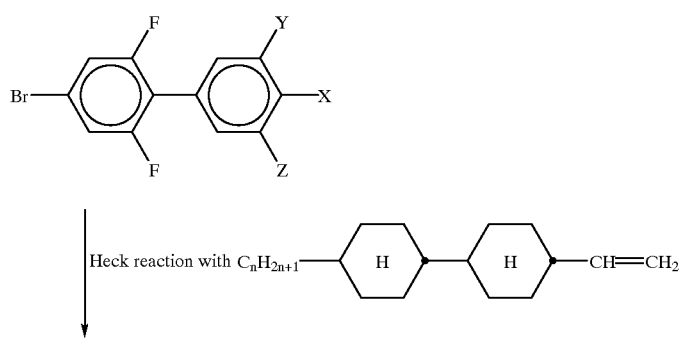

-continued
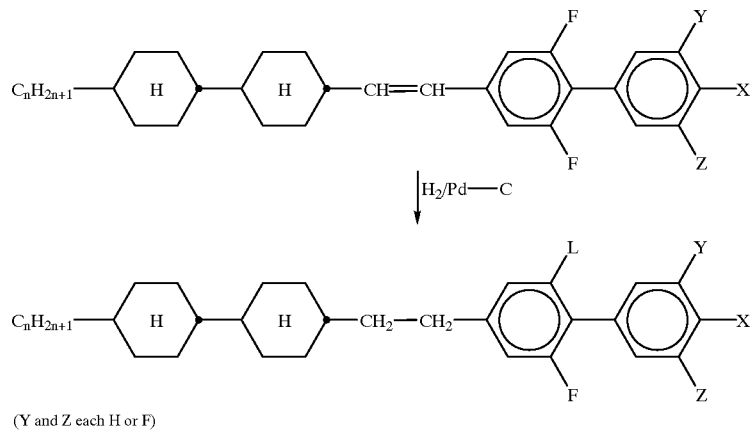
(Y and Z each H or F)
Scheme 4
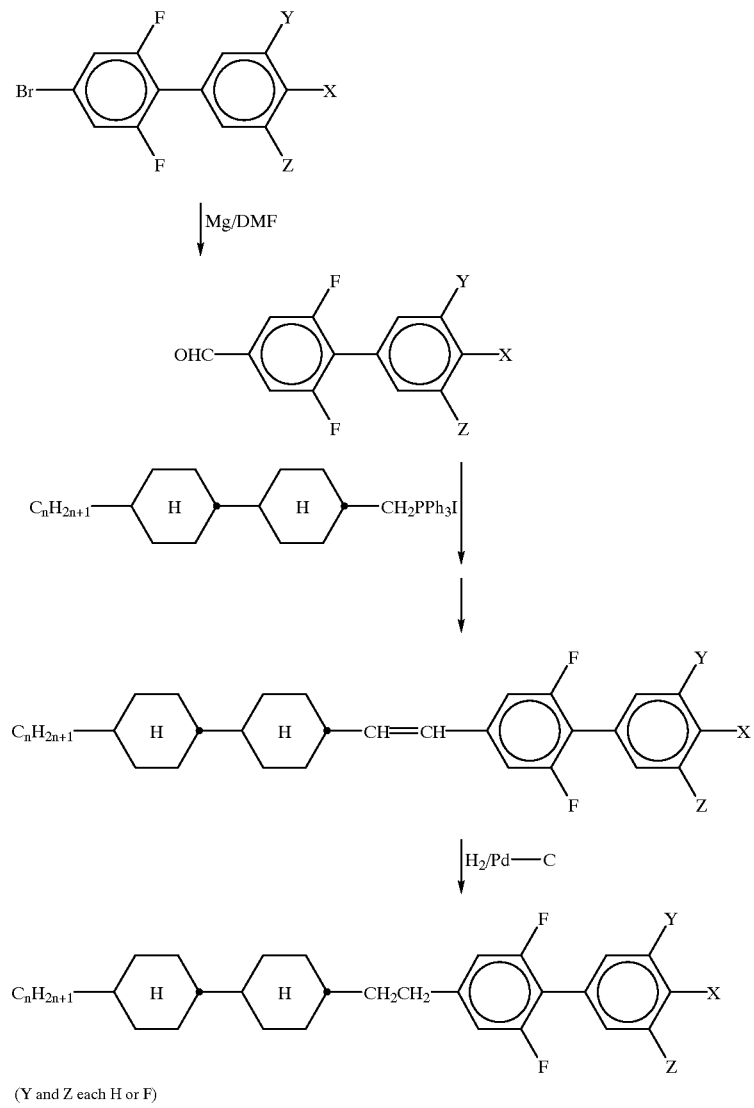
(Y and Z each H or F)

Scheme 5
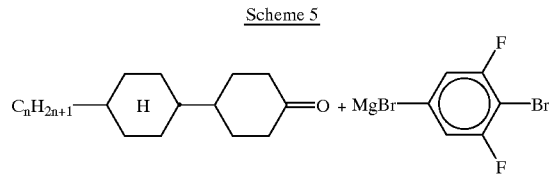
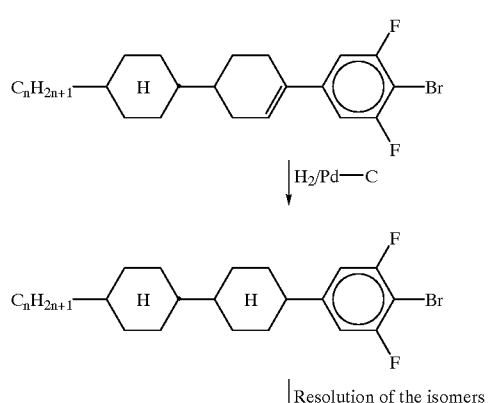
Resolution of the isomers
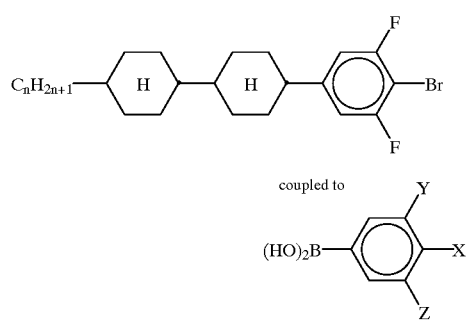
coupled to
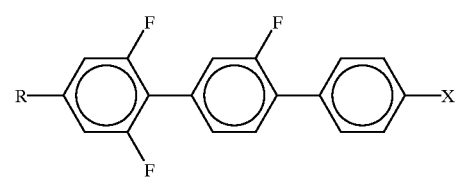
-continued
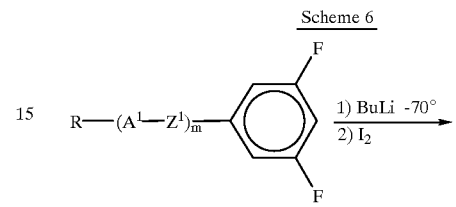
(Y and Z each H or F)
Scheme 6
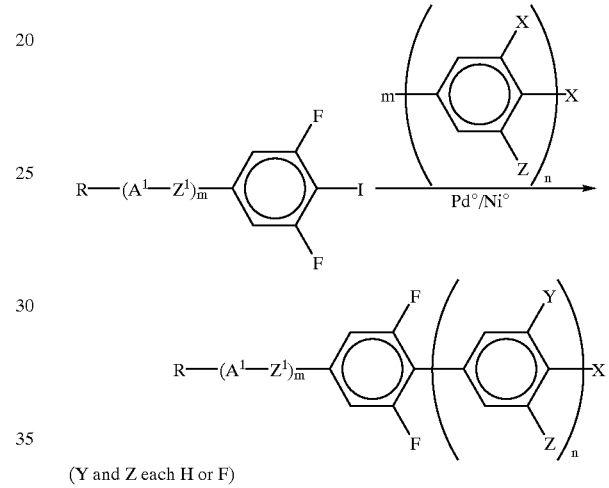
(Y and Z each H or F)
Some particularly preferred, smaller groups of compounds of the formula I are given below:
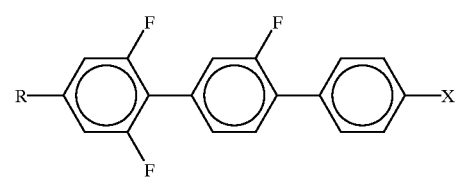
I1
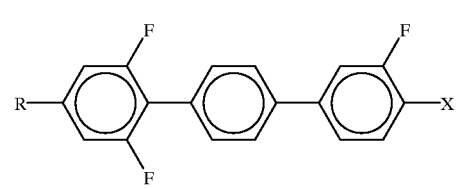
I2
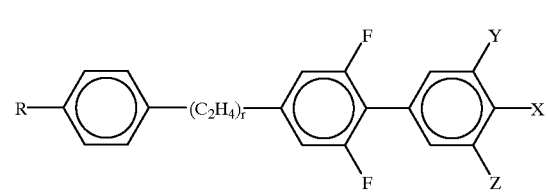
I3

-continued
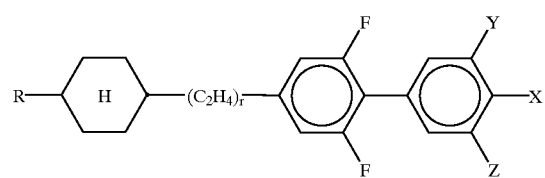
I4
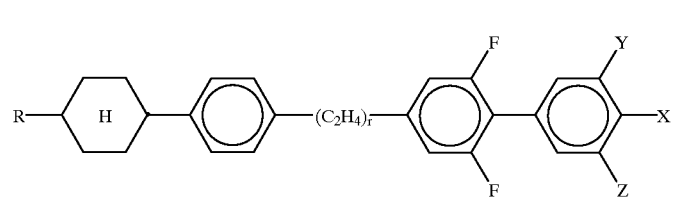
I5
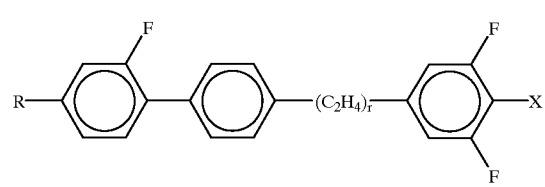
I6
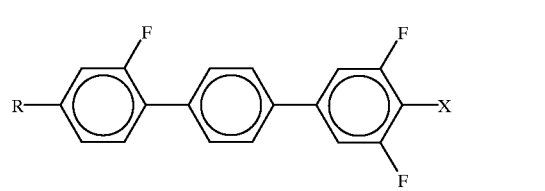
I7
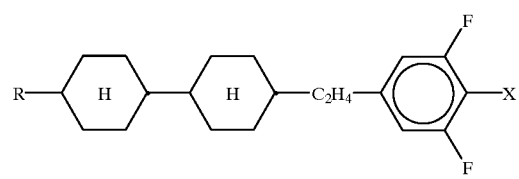
I8
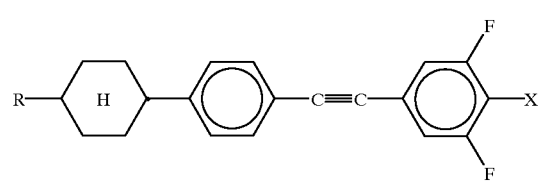
I9
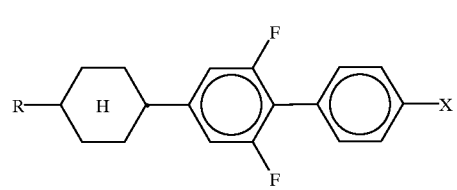
I10
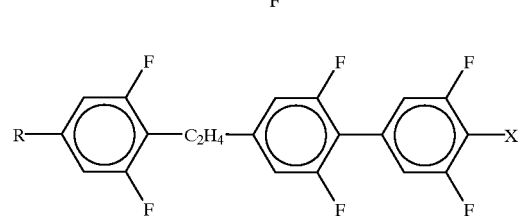
I11

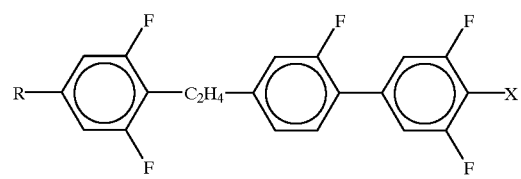
I12
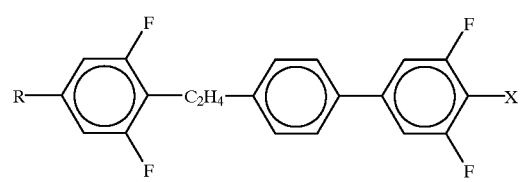
I13
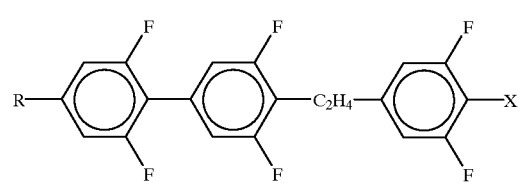
I14
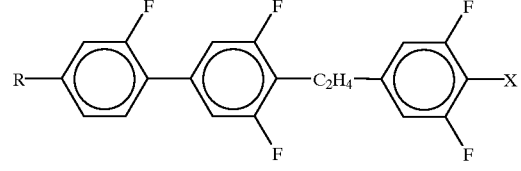
I15
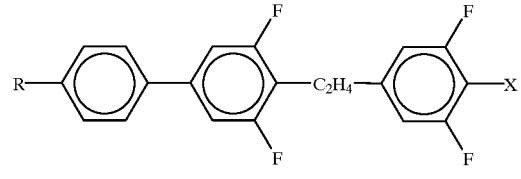
I16
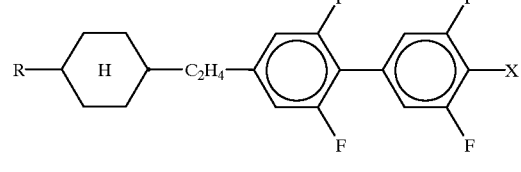
I17
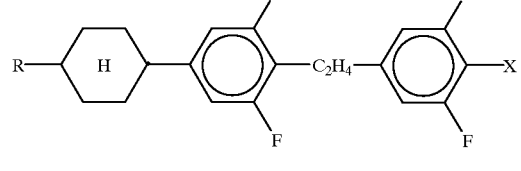
I18
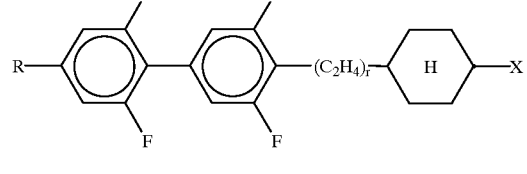
I19

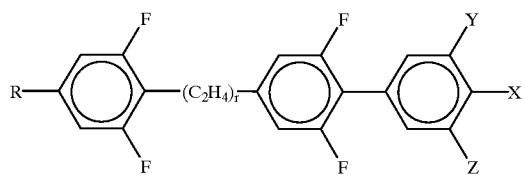

(r=0 or 1, Y and Z each H or F)

In formula 18, X is preferably R.

Particular preference is also given to compounds according to the invention in which one of the radicals $Z^1$ and $Z^2$ is —CH=CH—. These can be prepared, for example, in accordance with the following scheme:

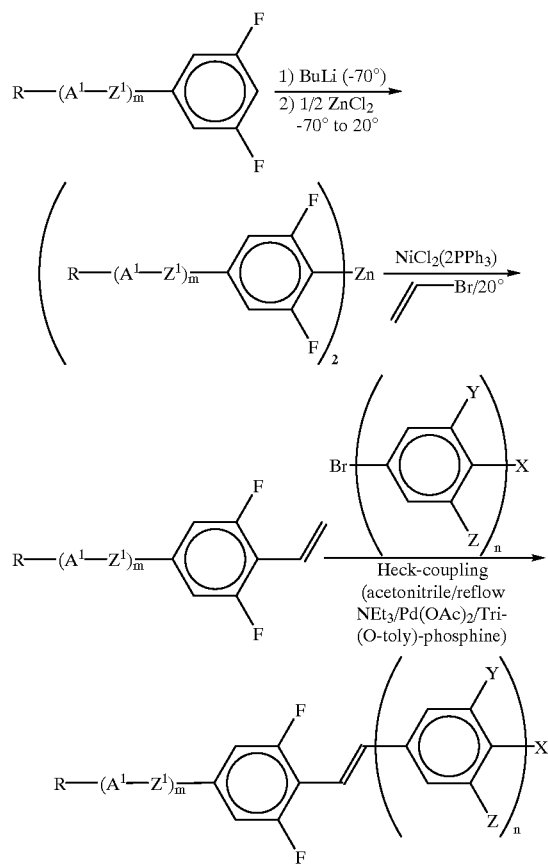

(Y and Z each H or F)

Corresponding compounds containing —CH$_2$CH$_2$— in place of —CH=CH— can also be obtained by hydrogenation on Pd/C or PtO$_2$ at 1–4 bar.

Particular preference is given to compounds of the formula I, in which one of the radicals $Z^1$ and $Z^2$ is —CO—O—, —O—CO—, —CH$_2$CH$_2$—, —CH=CH— or —C≡C— and the other radicals $Z^1$ and $Z^2$ are a single bond.

Particularly preferred tolan derivatives can be prepared in accordance with the following schemes analogously to the known Heck coupling reactions:

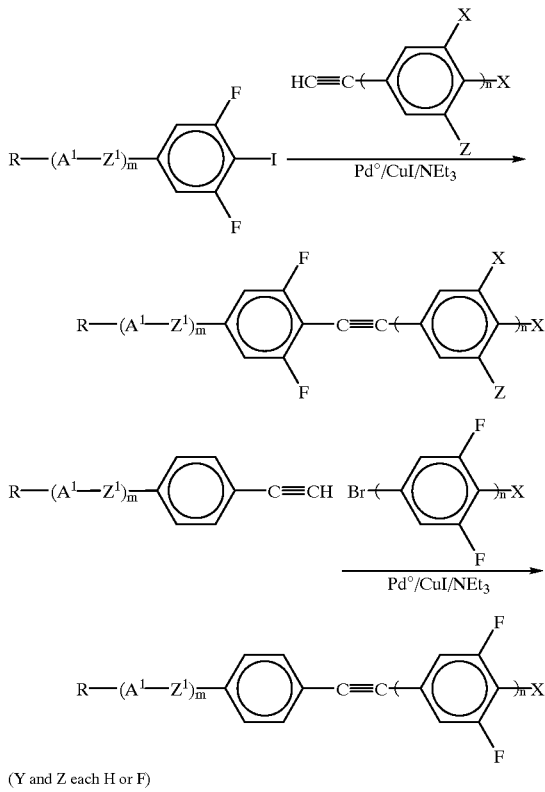

(Y and Z each H or F)

Further details on the synthesis or on corresponding precursors are given in the International Patent Applications PCT/EP 90/01471, PCT/EP 90/01437 and WO 90/08757.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenylor cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

R'—L—E—R''      1

R'—L—COO—E—R''   2

R'—L—OOC—E—R''   3

R'—L—$CH_2CH_2$—E—R''  4

R'—L—C≡C—E—R''   5

In the formulae 1, 2, 3, 4 and 5, L and E, which may be identical or different, are, in each case independently of one another, a bivalent radical from the group formed by -Phe-, -Cyc-, -Phe-Phe, -Phe-Cyc-, -Cyc-Cyc-, -Pyr-, -Dio-, -G-Phe- and -G-Cyc- and their mirror images, where Phe is unsubstituted or fluorine substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the sub-formulae 1a, 2a, 3a, 4a and 5a, R' and R'' are, in each case independently of one another, alkyl, alkenyl, alkoxy, alkenyloxy or alkanoyloxy having up to 8 carbon atoms. In most of these compounds, R' and R'' are different from one another, one of these radicals usually being alkyl or alkenyl. In the compounds of the sub-formulae 1b, 2b, 3b, 4b and 5b, R'' is —CN, —$CF_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also preferably contain components from the group comprising the compounds 1b, 2b, 3b, 4b and 5b (Group 2), whose proportions are preferably as follows:

Group 1: 20 to 90%, in particular 30 to 90%,

Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. Above and below, percentages are percent by weight. Temperatures are given in degrees Celsius. Mp. denotes melting point, Bp.=clear point. Furthermore, C=crystalline stage, N=nematic phase, S=smectic phase arid I=isotropic phase. The data between these symbols represent the transition temperatures. Δn denotes optical anisotropy (589 nm, 20° C.), and the viscosity ($mm^2$/sec) was determined at 20° C.

"Customary work-up" means that water is added if necessary, the mixture is extracted with methylene chloride, diethyl ether or toluene, the organic phase is separated off, dried and evaporated, the product is purified by distillation under reduced pressure or crystallization and/or chromatography. The following abbreviations are used:

| | |
|---|---|
| DAST | Diethylaminosulfur trifluoride |
| DCC | Dicyclohexylcarbodiimide |
| DDQ | Dichlorodicyanobenzoquinone |
| DIBALH | Diisobutylaluminum hydride |
| KOT | Potassium tertiary-butoxide |
| THF | Tetrahydrofuran |
| pTSOH | p-Toluenesulfonic acid |
| TMEDA | Tetramethylethylenediamine |

In the present application and in the examples below, the structures of the liquid-crystal compounds are indicated by acronyms, the transformation into chemical formulae taking place in accordance with Tables A and B below. All the radicals $C_nH_{2n+1}$ and $C_mH_{2m+1}$ are straight-chain alkyl radicals containing n or m carbon atoms respectively. The coding in Table B needs no explanation. In Table A, only the acronym for the parent structure is given. In individual cases, the acronym for the parent structure is followed, separated by a dash, by a code for the substituents $R^1$, $R^2$, $L^1$ and $L^2$:

| Code for $R^1$, $R^1$ $R^2$, $L^1$, $L^2$ | $R^2$ | $L^1$ | $L$ | | Code for $R^1$, $R^1$ $R^2$, $L^1$, $L^2$ | $R^2$ | $L^1$ | $L$ |
|---|---|---|---|---|---|---|---|---|
| nm | $C_nH_{2n+1}$ | $C_mH_{2m+1}$ | H | H | nmF | $C_nH_{2n+1}$ | $C_mH_{2m+1}$ | F | H |
| nOm | $C_nH_{2n+1}$ | $OC_mH_{2m+1}$ | H | H | nCF$_3$ | $C_nH_{2n+1}$ | CF$_3$ | H | H |
| nO.m | $OC_nH_{2n+1}$ | $C_mH_{2m+1}$ | H | H | nOCF$_3$ | $C_nH_{2n+1}$ | OCF$_3$ | H | H |
| nT | $C_nH_{2n+1}$ | CN | H | H | nOCF$_2$ | $C_nH_{2n+1}$ | OCHF$_2$ | H | H |
| nN.F | $C_nH_{2n+1}$ | CN | H | F | nS | $C_nH_{2n+1}$ | NCS | H | H |
| nF | $C_nH_{2n+1}$ | F | H | H | rVsN | $C_4H_{2r+1}$-CH=CH—$C_sH_{2s}$— | CN | H | H |
| nOF | $OC_nH_{2n+1}$ | F | H | H | rEsN | $C_rH_{24+1}$-O—$C_sH_{2s}$— | CN | H | H |
| nCl | $C_nH_{2n+1}$ | Cl | H | H | nNF | $C_nH_{2n+1}$ | CN | F | H |
| nF.F | $C_nH_{2n+1}$ | F | H | F | nAm | $C_nH_{2n+1}$ | $COOC_mH_{2m+1}$ | H | H |
| nOmFF | $C_nH_{2n+1}$ | $OC_mH_{2m+1}$ | F | F | | | | | |

TABLE A

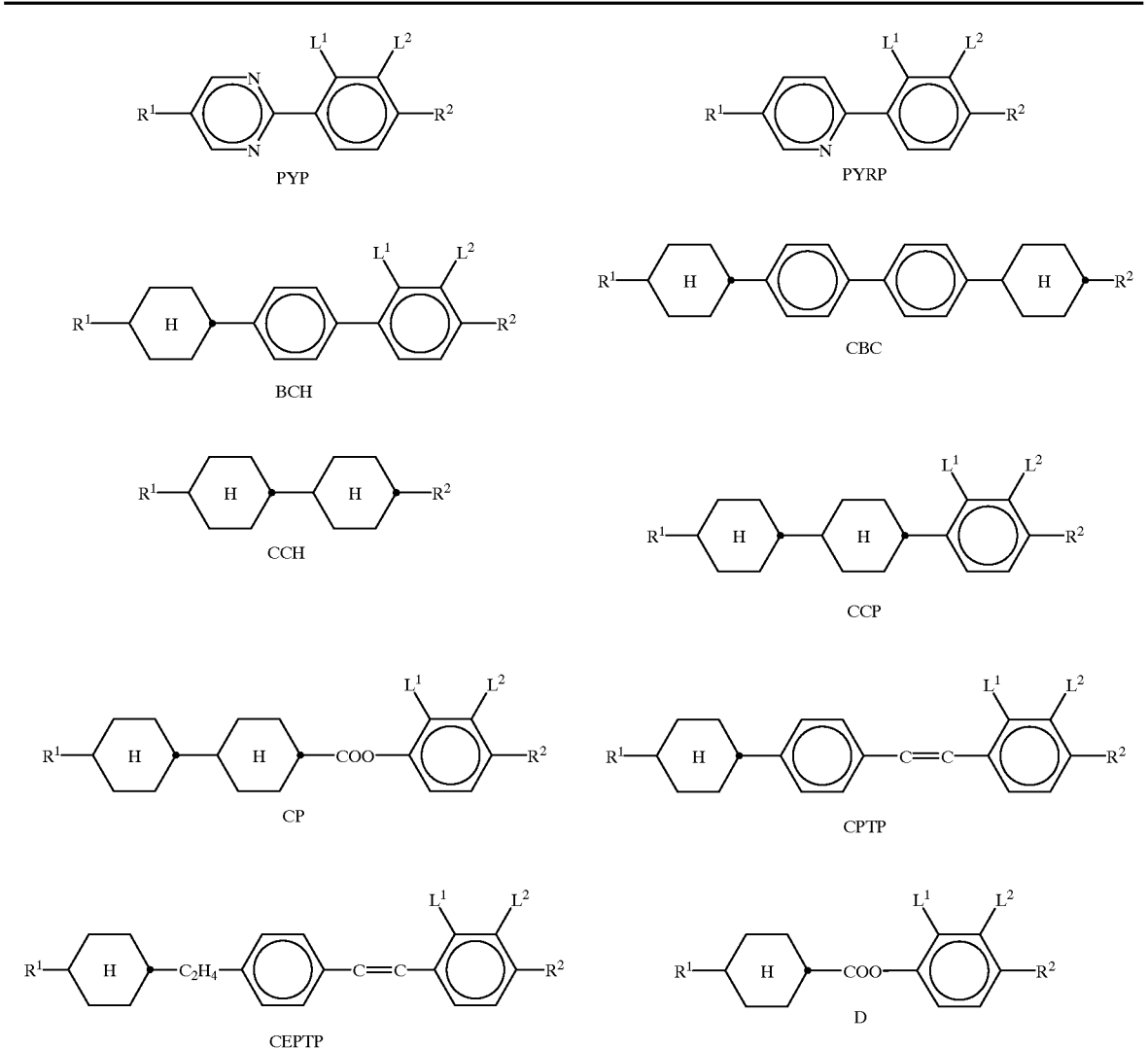

TABLE A-continued
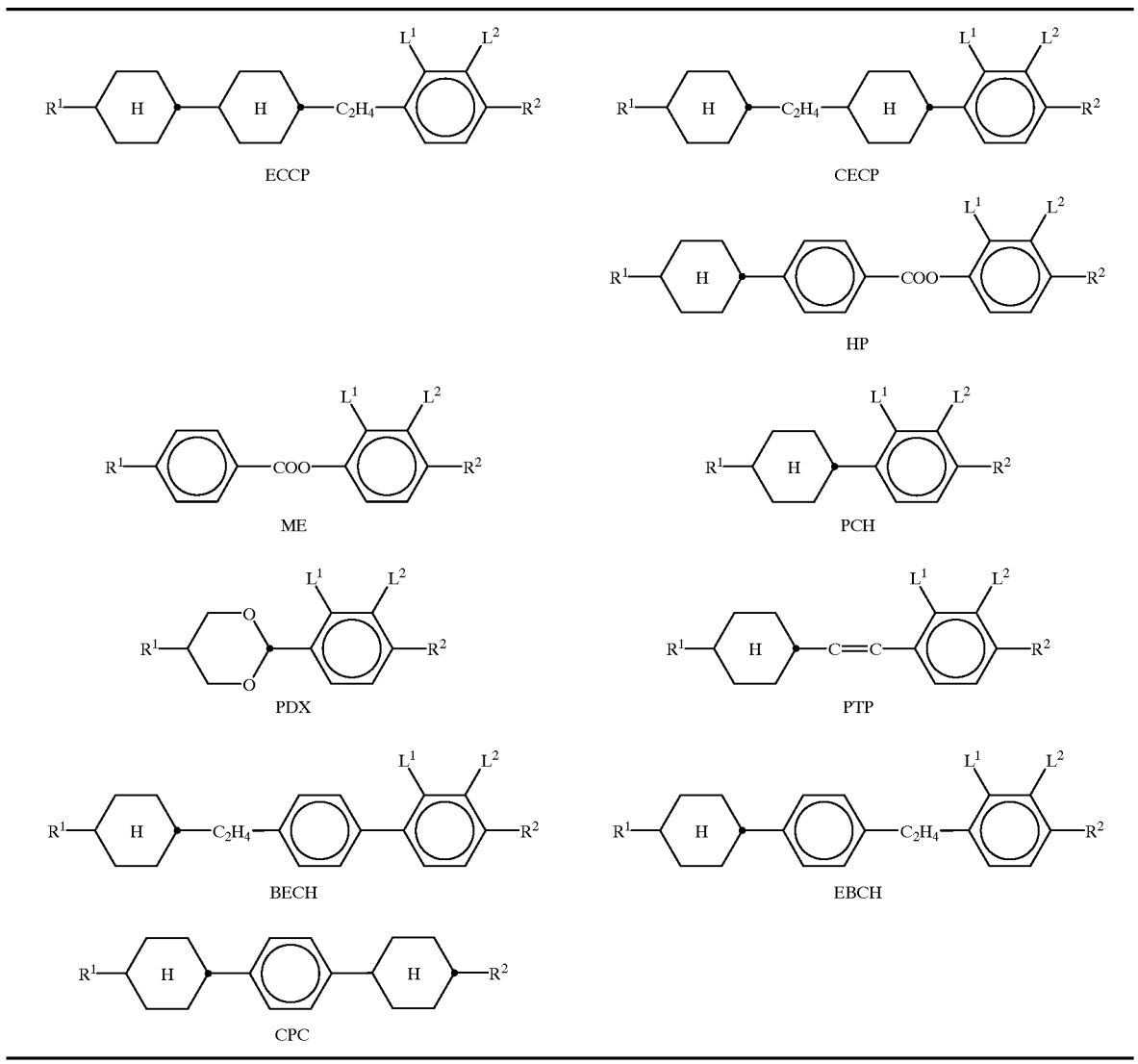
TABLE B
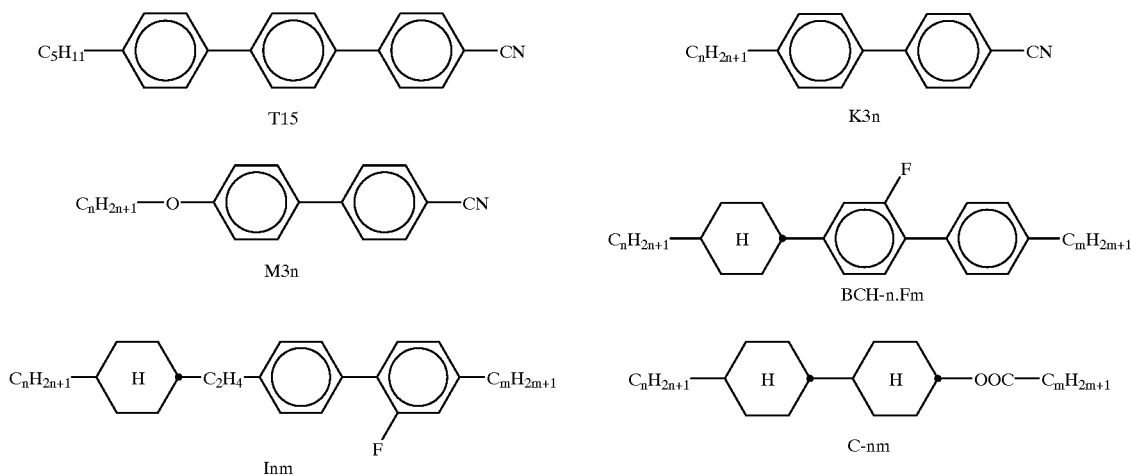

TABLE B-continued
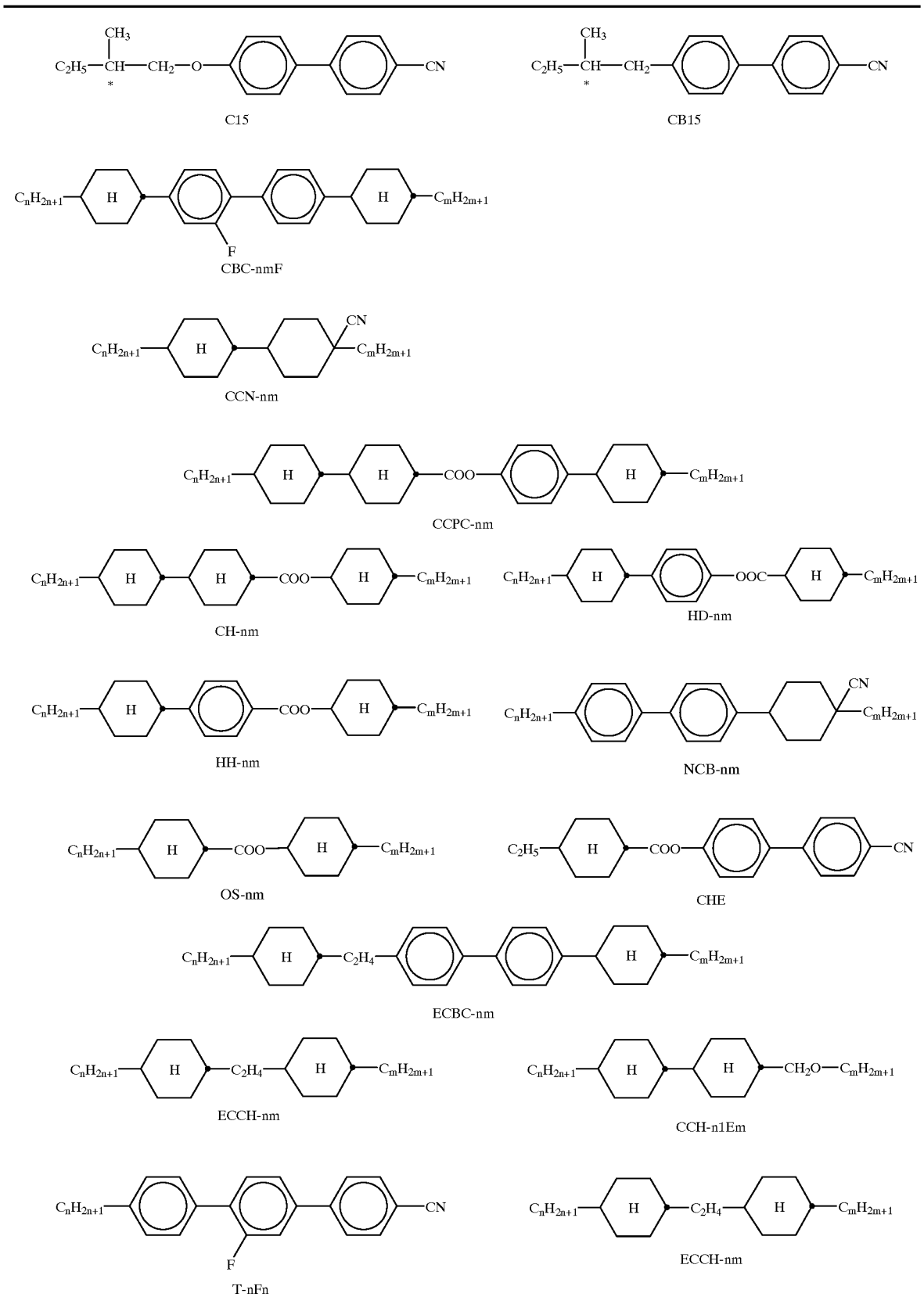

TABLE B-continued

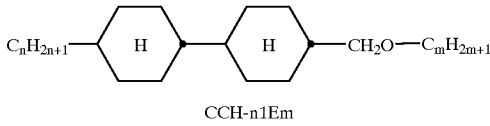
CCH-n1Em

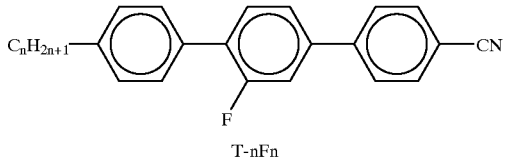
T-nFn

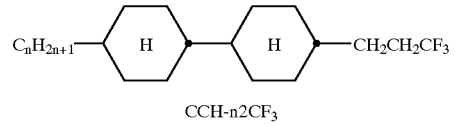
CCH-n2CF₃

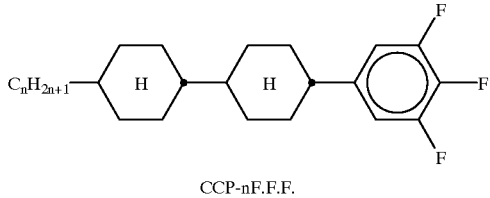
CCP-nF.F.F.

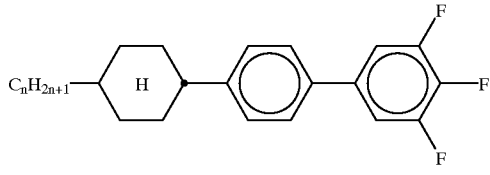
BCH-nF.F.F

EXAMPLE 1

A mixture of 9.2 g of 2,6-difluoro-4-[2-(p-ethoxyphenyl)ethyl]phenylboric acid (prepared by reacting 3,5-difluorobenzaldehyde with p-ethoxybenzyltriphenylphosphonium iodide by the Wittig method and subsequently hydrogenating the resultant styrene derivative on Pd/C), 5.9 g of 1-bromo-3,4-difluorobenzene, 38 ml of 2 molar aqueous $Na_2CO_3$ solution, 0.6 g of tetrakis(triphenylphosphine)palladium(0) and 75 ml of toluene is refluxed for two hours. The aqueous phase is extracted twice with toluene and combined with the organic phase. Customary aqueous work-up and chromatographic purification of the residue give 4-[2-(p-ethoxyphenyl)ethyl]-2,6,3',4'-tetrafluorobiphenyl, C 92 I, Δε+24.

EXAMPLES 2 TO 58

The following compounds according to the invention are obtained from the appropriate precursors of the formula II analogously to one of the two schemes on page 12:

| | R | $(A^1-Z^1)_m$ | $(Z^2-A^2)_m$ | X |
|---|---|---|---|---|
| (2) | n-Propyl | 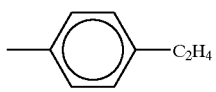 | 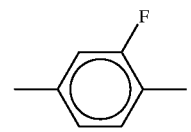 | F |
| (3) | n-Pentyl | 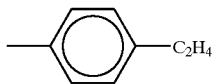 | 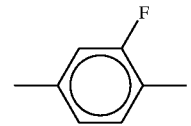 | F |
| (4) | n-Proyl | 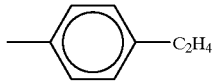 | 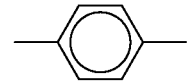 | OCF₃ |
| (5) | n-Pentyl | 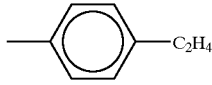 | 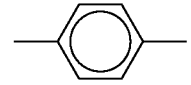 | OCF₃ |

-continued
| | R | (A¹-Z¹)ₘ | (Z²-A²)ₘ | X |
|---|---|---|---|---|
| (6) | n-Propyl | 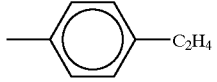 |  | F |
| (7) | n-Propyl | 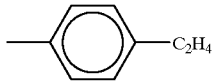 |  | Cl |
| (8) | n-Propyl | 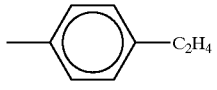 | 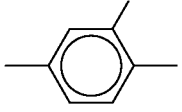 | Cl |
| (9) | n-Propyl | 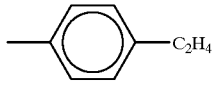 | 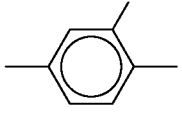 | CN |
| (10) | n-Propyl | 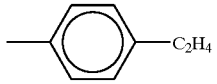 |  | CN |
| (11) | n-Propyl | 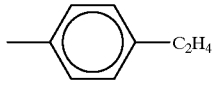 |  | CF₃ |
| (12) | n-Propyl | 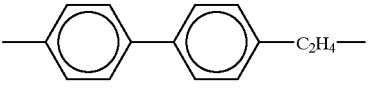 |  | OCF₃ |
| (13) | n-Propyl | 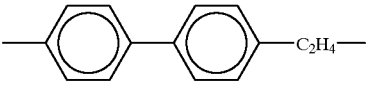 |  | CF₃ |
| (14) | n-Propyl | 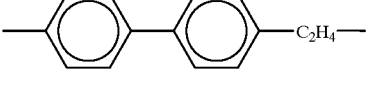 |  | CN |
| (15) | n-Propyl | 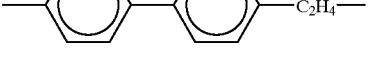 |  | F |
| (16) | n-Propyl |  |  | OCF₃ |
| (17) | n-Propyl |  |  | CF₃ |
| (18) | n-Propyl | 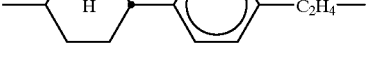 |  | CN |

-continued
| | R | (A¹-Z¹)ₘ | (Z²-A²)ₘ | X |
|---|---|---|---|---|
| (19) | n-Propyl | 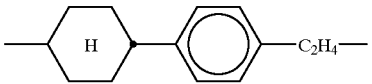 |  | F |
| (20) | n-Propyl | 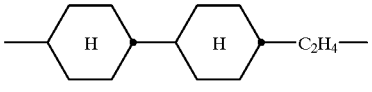 |  | OCF₃ |
| (21) | n-Propyl | 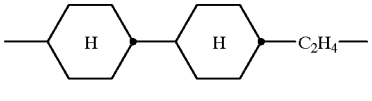 |  | CF₃ |
| (22) | n-Propyl | 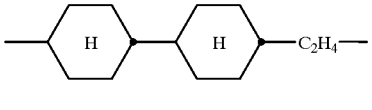 |  | CN |
| (23) | n-Propyl | 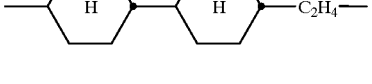 |  | F |
| (24) | n-Propyl | 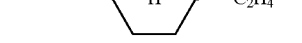 |  | OCF₃ |
| (25) | n-Propyl | 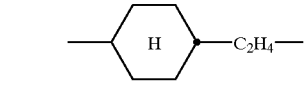 | 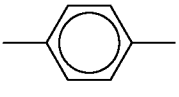 | CF₃ |
| (26) | n-Propyl | 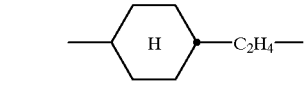 |  | CN |
| (27) | n-Propyl | 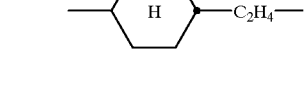 |  | F |
| (28) | n-Pentyl |  |  | CN, C¹²⁴ N¹⁵¹ I |
| (29) | n-Pentyl |  |  | F |
| (30) | n-Pentyl |  |  | CF₃ |
| (31) | n-Pentyl |  |  | OCF₃ |
| (32) | n-Pentyl | 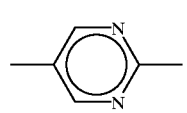 | 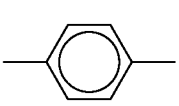 | CN |

-continued

| | R | (A¹-Z¹)ₘ | (Z²-A²)ₘ | X |
|---|---|---|---|---|
| (33) | n-Pentyl | pyrimidine (2,5-diyl, N at 1,3) | phenylene | F |
| (34) | n-Pentyl | pyrimidine (2,5-diyl, N at 1,3) | phenylene | $CF_3$ |
| (35) | n-Pentyl | pyrimidine (2,5-diyl, N at 1,3) | phenylene | $OCF_3$ |
| (36) | n-Pentyl | pyridine (2,5-diyl) | phenylene | CN |
| (37) | n-Pentyl | pyridine (2,5-diyl) | phenylene | F |
| (38) | n-Pentyl | pyridine (2,5-diyl) | phenylene | $CF_3$ |
| (39) | n-Pentyl | pyridine (2,5-diyl) | phenylene | $OCF_3$ |
| (40) | n-Propyl | — | —$C_2H_4$—biphenylene— | CN |
| (41) | n-Propyl | — | —$C_2H_4$—biphenylene— | $CF_3$ |
| (42) | n-Propyl | — | —$C_2H_4$—biphenylene— | F |
| (43) | n-Propyl | — | —$C_2H_4$—biphenylene— | $OCF_3$ |
| (44) | n-Propyl | 2,3-difluoro-phenylene | phenylene | $OCF_3$ |

-continued

| | R | $(A^1-Z^1)_m$ | $(Z^2-A^2)_m$ | X |
|---|---|---|---|---|
| (45) | n-Propyl | cyclohexyl (H) | 3-fluorophenyl | F |
| (46) | n-Propyl | cyclohexyl (H) | phenyl | CN |
| (47) | n-Propyl | cyclohexyl (H) | phenyl | $CF_3$ |
| (48) | n-Propyl | cyclohexyl (H) | phenyl | $OCF_3$ |
| (49) | n-Propyl | cyclohexyl (H) | phenyl | F |
| (50) | Ethoxy | phenyl-$C_2H_4$- | phenyl | $OCF_3$, C 112 I |
| (51) | Ethoxy | phenyl-$C_2H_4$- | phenyl | F, C 102 I |
| (52) | n-Propyl | — | biphenyl | CN |
| (53) | n-Propyl | — | biphenyl | F |
| (54) | n-Propyl | — | pyrimidinyl-phenyl | F |
| (55) | n-Propyl | — | pyrimidinyl-phenyl | CN |
| (56) | n-Propyl | — | pyrimidinyl-phenyl | $OCF_3$ |
| (57) | n-Pentyl | — | phenyl | $OCF_3$, C-4 I |

-continued

| | R | $(A^1-Z^1)_m$ | $(Z^2-A^2)_m$ | X |
|---|---|---|---|---|
| (57A) | Ethoxy | — | ⌬ | $OCF_3$, C 44 I |
| (58) | n-Pentyl | — | ⌬ | $CF_3$, C 35 I |
| (58a) | Ethoxy | — | ⌬ | $CF_2$ C 75 I |

EXAMPLE 59

A solution of 0.1 mol of p-bromotrifluoromethoxybenzene in 100 ml of THF is added dropwise to a suspension of 0.1 mol of Mg turnings in 50 ml of THF at such a rate that the reaction mixture boils gently. After the mixture has been stirred for one hour, 0.1 mol of trimethyl borate is added dropwise at room temperature, and the mixture is stirred for a further hour and hydrolyzed using dilute hydrochloric acid. After extractive work-up, the resultant boric acid (0.05 mol) is refluxed for two hours together with 0.05 mol of 4-(trans-4-n-pentyl cyclohexyl)-2,6-difluoroiodobenzene [obtainable by reacting 4-pentylcyclohexanone with 3,5-difluorophenylmagnesium bromide, eliminating water, and hydrogenating the cyclohexenebenzene on Pd/C. The resultant 3,5-difluoropenyl [sic] compound is metallated at –70° in THF/TMEDA using n-BuLi and subsequently reacted with iodine in THF at –70°], 38 ml of 2 molar aqueous $Na_2CO_3$ solution, 0.6 g of tetrakis(triphenylphosphine)palladium(0) and 75 ml of toluene. Customary aqueous work-up and chromatographic purification give 4-(trans-4-n-pentylcyclohexyl)-2,6-difluoro-4'-trifluoromethoxybiphenyl.

The preferred compounds of the formula

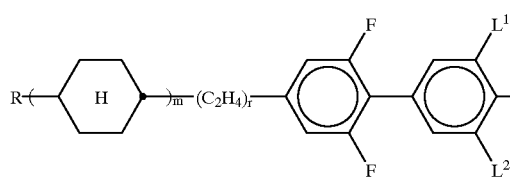

in which R, m, and X are as defined for the formula I, and r is 0 or 1 and $L^1$ and $L^2$ are, in each case independently of one another, H or F, are obtained analogously from the corresponding difluoroiodo derivatives and boric acid.

| Example | R | m | r | X | L | $L^2$ |
|---|---|---|---|---|---|---|
| (60) | Ethyl | 1 | 0 | $OCF_3$ | H | H |
| (61) | Propyl | 1 | 0 | $OCF_3$ | H | H |
| (62) | Butyl | 1 | 0 | $OCF_3$ | H | H |
| (63) | Ethyl | 1 | 1 | $OCF_3$ | H | H |
| (64) | Propyl | 1 | 1 | $OCF_3$ | H | H |
| (65) | Butyl | 1 | 1 | $OCF_3$ | H | H |

-continued

| Example | R | m | r | X | L | $L^2$ |
|---|---|---|---|---|---|---|
| (66) | Pentyl | 1 | 1 | $OCF_3$ | H | H, C 49 N 68,5 I |
| (67) | Ethyl | 2 | 0 | $OCF_3$ | H | H |
| (68) | Propyl | 2 | 0 | $OCF_3$ | H | H, C 112 N 270 I |
| (69) | Butyl | 2 | 0 | $OCF_3$ | H | H |
| (70) | Pentyl | 2 | 0 | $OCF_3$ | H | H |
| (71) | Ethyl | 2 | 1 | $OCF_3$ | H | H |
| (72) | Propyl | 2 | 1 | $OCF_3$ | H | H, C 91 N 213 I |
| (73) | Butyl | 2 | 1 | $OCF_3$ | H | H |
| (74) | Pentyl | 2 | 1 | $OCF_3$ | H | H |
| (75) | Ethyl | 1 | 0 | $CF_3$ | H | H |
| (76) | Propyl | 1 | 0 | $CF_3$ | H | H |
| (77) | Butyl | 1 | 0 | $CF_3$ | H | H |
| (78) | Pentyl | 1 | 0 | $CF_3$ | H | H |
| (79) | Ethyl | 1 | 1 | $CF_3$ | H | H |
| (80) | Propyl | 1 | 1 | $CF_3$ | H | H |
| (81) | Butyl | 1 | 1 | $CF_3$ | H | H |
| (82) | Pentyl | 1 | 1 | $CF_3$ | H | H, C 93 I |
| (83) | Ethyl | 2 | 0 | $CF_3$ | H | H |
| (84) | Propyl | 2 | 0 | $CF_3$ | H | H |
| (85) | Butyl | 2 | 0 | $CF_3$ | H | H |
| (86) | Pentyl | 2 | 0 | $CF_3$ | H | H |
| (87) | Ethyl | 2 | 1 | $CF_3$ | H | H |
| (88) | Propyl | 2 | 1 | $CF_3$ | H | H |
| (89) | Butyl | 2 | 1 | $CF_3$ | H | H |
| (90) | Pentyl | 2 | 1 | $CF_3$ | H | H |
| (91) | Ethyl | 1 | 0 | F | H | H |
| (92) | Propyl | 1 | 0 | F | H | H |
| (93) | Butyl | 1 | 0 | F | H | H |
| (94) | Pentyl | 1 | 0 | F | H | H, C 100 N (64) I |
| (95) | Ethyl | 1 | 1 | F | H | H |
| (96) | Propyl | 1 | 1 | F | H | H |
| (97) | Butyl | 1 | 1 | F | H | H |
| (98) | Pentyl | 1 | 1 | F | H | H, C 91 I viscosity 18.8 cSt |
| (99) | Ethyl | 2 | 0 | F | H | H |
| (100) | Propyl | 2 | 0 | F | H | H |
| (101) | Butyl | 2 | 0 | F | H | H |
| (102) | Pentyl | 2 | 0 | F | H | H |
| (103) | Ethyl | 2 | 1 | F | H | H |
| (104) | Propyl | 2 | 1 | F | H | H, C 140 N 212 I |
| (105) | Butyl | 2 | 1 | F | H | H |
| (106) | Pentyl | 2 | 1 | F | H | H |
| (107) | Ethyl | 1 | 0 | F | F | H |
| (108) | Propyl | 1 | 0 | F | F | H, C 81 I, Δε 11.0 |
| (109) | Butyl | 1 | 0 | F | F | H |
| (110) | Pentyl | 1 | 0 | F | F | H |
| (111) | Ethyl | 1 | 1 | F | F | H |
| (112) | Propyl | 1 | 1 | F | F | H |
| (113) | Butyl | 1 | 1 | F | F | H |
| (114) | Pentyl | 1 | 1 | F | F | H, C 40 N 46.6 I |
| (115) | Ethyl | 2 | 0 | F | F | H |

-continued

| Example | R | m | r | X | L | L² |
|---|---|---|---|---|---|---|
| (116) | Propyl | 2 | 0 | F | F | H, C 133 N 242 I Δε 12.3 |
| (117) | Butyl | 2 | 0 | F | F | H |
| (118) | Pentyl | 2 | 0 | F | F | H |
| (119) | Ethyl | 2 | 1 | F | F | H |
| (120) | Propyl | 2 | 1 | F | F | H |
| (121) | Butyl | 2 | 1 | F | F | H |
| (122) | Pentyl | 2 | 1 | F | F | H |
| (123) | Ethyl | 1 | 0 | F | F | F |
| (124) | Propyl | 1 | 0 | F | F | F |
| (125) | Butyl | 1 | 0 | F | F | F |
| (126) | Pentyl | 1 | 0 | F | F | F |
| (127) | Ethyl | 1 | 1 | F | F | F |
| (128) | Propyl | 1 | 1 | F | F | F |
| (129) | Butyl | 1 | 1 | F | F | F |
| (130) | Pentyl | 1 | 1 | F | F | F, C 65.5 I |
| (131) | Ethyl | 2 | 0 | F | F | F |
| (132) | Propyl | 2 | 0 | F | F | F |
| (133) | Butyl | 2 | 0 | F | F | F |
| (134) | Pentyl | 2 | 0 | F | F | F, C 156 N211 I |
| (135) | Ethyl | 2 | 1 | F | F | F |
| (136) | Propyl | 2 | 1 | F | F | F |
| (137) | Butyl | 2 | 1 | F | F | F |
| (138) | Pentyl | 2 | 1 | F | F | F |
| (139) | Ethyl | 1 | 0 | Cl | H | H |
| (140) | Propyl | 1 | 0 | Cl | H | H |
| (141) | Butyl | 1 | 0 | Cl | H | H |
| (142) | Pentyl | 1 | 0 | Cl | H | H |
| (143) | Ethyl | 1 | 1 | Cl | H | H |
| (144) | Propyl | 1 | 1 | Cl | H | H |
| (145) | Butyl | 1 | 1 | Cl | H | H |
| (146) | Pentyl | 1 | 1 | Cl | H | H, C 54 N 91 I |
| (147) | Ethyl | 2 | 0 | Cl | H | H |
| (148) | Propyl | 2 | 0 | Cl | H | H |
| (149) | Butyl | 2 | 0 | Cl | H | H |
| (150) | Pentyl | 2 | 0 | Cl | H | H |
| (151) | Ethyl | 2 | 1 | Cl | H | H |
| (152) | Propyl | 2 | 1 | Cl | H | H |
| (153) | Butyl | 2 | 1 | Cl | H | H |
| (154) | Pentyl | 2 | 1 | Cl | H | H |
| (155) | Ethyl | 1 | 0 | Cl | F | H |
| (156) | Propyl | 1 | 0 | Cl | F | H |
| (157) | Butyl | 1 | 0 | Cl | F | H |
| (158) | Pentyl | 1 | 0 | Cl | F | H |
| (159) | Ethyl | 1 | 1 | Cl | F | H |
| (160) | Propyl | 1 | 1 | Cl | F | H |
| (161) | Butyl | 1 | 1 | Cl | F | H |
| (162) | Pentyl | 1 | 1 | Cl | F | H, C 47 N 74 I Δε 8.8 |
| (163) | Ethyl | 2 | 0 | Cl | F | H |
| (164) | Propyl | 2 | 0 | Cl | F | H |
| (165) | Butyl | 2 | 0 | Cl | F | H |
| (166) | Pentyl | 2 | 0 | Cl | F | H |
| (167) | Ethyl | 2 | 1 | Cl | F | H |
| (168) | Propyl | 2 | 1 | Cl | F | H |
| (169) | Butyl | 2 | 1 | Cl | F | H |
| (170) | Pentyl | 2 | 1 | Cl | F | H |
| (171) | Ethyl | 1 | 0 | Cl | F | F |
| (172) | Propyl | 1 | 0 | Cl | F | F |
| (173) | Butyl | 1 | 0 | Cl | F | F |
| (174) | Pentyl | 1 | 0 | Cl | F | F |
| (175) | Ethyl | 1 | 1 | Cl | F | F |
| (176) | Propyl | 1 | 1 | Cl | F | F |
| (177) | Butyl | 1 | 1 | Cl | F | F |
| (178) | Pentyl | 1 | 1 | Cl | F | F C 66 I |
| (179) | Ethyl | 2 | 0 | Cl | F | F (N60.3I) |
| (180) | Propyl | 2 | 0 | Cl | F | F |
| (181) | Butyl | 2 | 0 | Cl | F | F |
| (182) | Pentyl | 2 | 0 | Cl | F | F |
| (183) | Ethyl | 2 | 1 | Cl | F | F |
| (184) | Propyl | 2 | 1 | Cl | F | F |
| (185) | Butyl | 2 | 1 | Cl | F | F |
| (186) | Pentyl | 2 | 1 | Cl | F | F |
| (187) | Ethyl | 1 | 0 | CN | H | H |
| (188) | Propyl | 1 | 0 | CN | H | H |
| (189) | Butyl | 1 | 0 | CN | H | H |
| (190) | Pentyl | 1 | 0 | CN | H | H |
| (191) | Ethyl | 1 | 1 | CN | H | H |
| (192) | Propyl | 1 | 1 | CN | H | H |
| (193) | Butyl | 1 | 1 | CN | H | H |
| (194) | Pentyl | 1 | 1 | CN | H | H, C 123 N 131 I |
| (195) | Ethyl | 2 | 0 | CN | H | H |
| (196) | Propyl | 2 | 0 | CN | H | H |
| (197) | Butyl | 2 | 0 | CN | H | H |
| (198) | Pentyl | 2 | 0 | CN | H | H |
| (199) | Ethyl | 2 | 1 | CN | H | H |
| (200) | Propyl | 2 | 1 | CN | H | H |
| (201) | Butyl | 2 | 1 | CN | H | H |
| (202) | Pentyl | 2 | 1 | CN | H | H |
| (203) | Ethyl | 1 | 0 | $OCF_3$ | F | H |
| (204) | Propyl | 1 | 0 | $OCF_3$ | F | H |
| (205) | Butyl | 1 | 0 | $OCF_3$ | F | H |
| (206) | Pentyl | 1 | 0 | $OCF_3$ | F | H |
| (207) | Ethyl | 1 | 1 | $OCF_3$ | F | H |
| (208) | Propyl | 1 | 1 | $OCF_3$ | F | H |
| (209) | Butyl | 1 | 1 | $OCF_3$ | F | H |
| (210) | Pentyl | 1 | 1 | $OCF_3$ | F | H |
| (211) | Ethyl | 2 | 0 | $OCF_3$ | F | H |
| (212) | Propyl | 2 | 0 | $OCF_3$ | F | H |
| (213) | Butyl | 2 | 0 | $OCF_3$ | F | H |
| (214) | Pentyl | 2 | 0 | $OCF_3$ | F | H |
| (215) | Ethyl | 2 | 1 | $OCF_3$ | F | H |
| (216) | Propyl | 2 | 1 | $OCF_3$ | F | H |
| (217) | Butyl | 2 | 1 | $OCF_3$ | F | H |
| (218) | Pentyl | 2 | 1 | $OCF_3$ | F | H |
| (219) | Ethyl | 1 | 0 | $OCF_3$ | F | F |
| (220) | Propyl | 1 | 0 | $OCF_3$ | F | F |
| (221) | Butyl | 1 | 0 | $OCF_3$ | F | F |
| (222) | Pentyl | 1 | 0 | $OCF_3$ | F | F |
| (223) | Ethyl | 1 | 1 | $OCF_3$ | F | F |
| (224) | Propyl | 1 | 1 | $OCF_3$ | F | F |
| (225) | Butyl | 1 | 1 | $OCF_3$ | F | F |
| (226) | Pentyl | 1 | 1 | $OCF_3$ | F | F |
| (227) | Ethyl | 2 | 0 | $OCF_3$ | F | F |
| (228) | Propyl | 2 | 0 | $OCF_3$ | F | F |
| (229) | Butyl | 2 | 0 | $OCF_3$ | F | F |
| (230) | Pentyl | 2 | 0 | $OCF_3$ | F | F |
| (231) | Ethyl | 2 | 1 | $OCF_3$ | F | F |
| (232) | Propyl | 2 | 1 | $OCF_3$ | F | F |
| (233) | Butyl | 2 | 1 | $OCF_3$ | F | F |
| (234) | Pentyl | 2 | 1 | $OCF_3$ | F | F |

EXAMPLE 235

A mixture of 9.2 g of 2,6-difluoro-4-[2-(p-ethoxyphenyl)ethyl]phenylboric acid (prepared by reacting 3,5-difluorobenzaldehyde with p-ethoxybenzyltriphenylphosphonium iodide by the Wittig method and subsequently hydrogenating the resulting styrene derivative on Pd/C), 6.0 g of 1-bromo-4-n-propylbenzene, 38 ml of 2 ml [sic] aqueous $Na_2CO_3$ solution, 0.6 g of tetrakis(triphenylphosphine)palladium(0) and 75 ml of toluene is refluxed for two hours. The aqueous phase is extracted twice with toluene and combined with the organic phase. Conventional aqueous work-up and chromatographic purification of the residue give 4-[2-(p-ethoxyphenyl)ethyl]-2,6-difluoro-4'-n-propylbiphenyl.

EXAMPLES 236 TO 242

The following compounds according to the invention are obtained analogously from the appropriate precursors of the formula II:

| | R | $(A^1-Z^1)_m$ | $(Z^2-A^2)_m$ | X |
|---|---|---|---|---|
| (236) | n-Propyl | 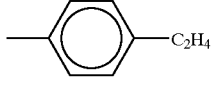 | 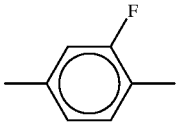 | Ethyl |
| (237) | n-Pentyl | 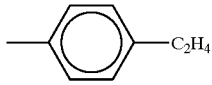 | 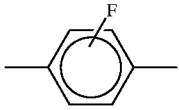 | Ethyl |
| (238) | n-Propyl | 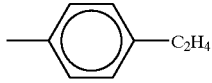 |  | Ethyl |
| (239) | n-Pentyl | 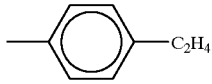 |  | Ethyl |
| (240) | n-Propyl | 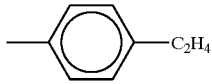 |  | n-Propyl |
| (241) | n-Propyl | 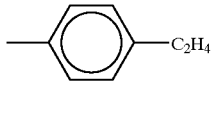 |  | n-Pentyl |
| (242) | n-Propyl |  | 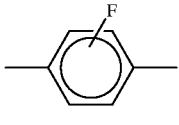 | n-Propyl |
| (243) | n-Propyl | 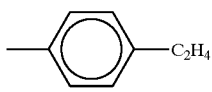 | 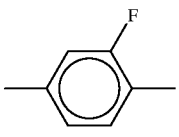 | n-Pentyl |
| (244) | n-Propyl | 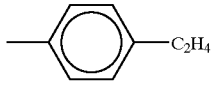 |  | Ethyl |
| (245) | n-Propyl |  |  | n-Propyl |
| (246) | n-Propyl | 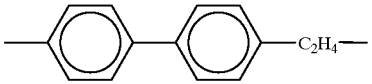 |  | Methyl |
| (247) | n-Propyl | 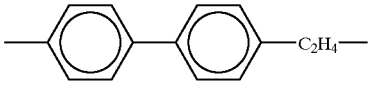 |  | Ethyl |
| (248) | n-Propyl | 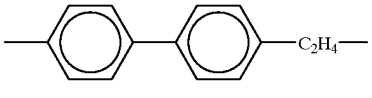 |  | n-Propyl |

-continued
| | R | (A¹-Z¹)ₘ | (Z²-A²)ₘ | X |
|---|---|---|---|---|
| (249) | n-Propyl | 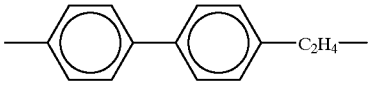 |  | n-Pentyl |
| (250) | n-Propyl | 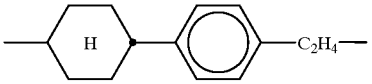 |  | Methyl |
| (251) | n-Propyl | 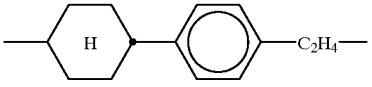 |  | Ethyl |
| (252) | n-Propyl | 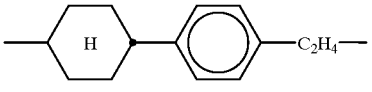 |  | n-Propyl |
| (253) | n-Propyl | 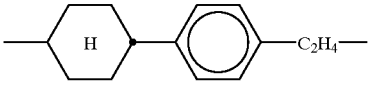 |  | Methoxy |
| (254) | n-Propyl | 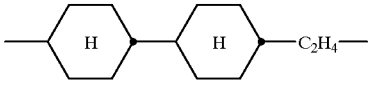 |  | Methyl |
| (255) | n-Propyl | 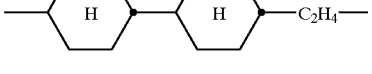 |  | Ethyl |
| (256) | n-Propyl | 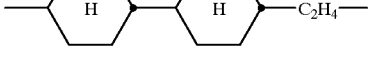 |  | n-Propyl |
| (257) | n-Propyl | 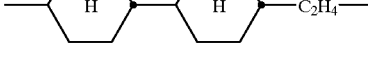 |  | n-Pentyl |
| (258) | n-Propyl | 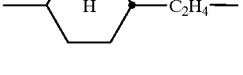 |  | Methyl |
| (259) | n-Propyl | 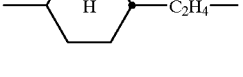 |  | Ethyl |
| (260) | n-Propyl | 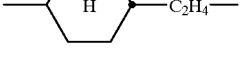 |  | n-Propyl |
| (261) | n-Propyl | 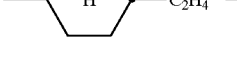 |  | n-Pentyl |

-continued

| | R | (A¹-Z¹)ₘ | (Z²-A²)ₘ | X |
|---|---|---|---|---|
| (262) | n-Pentyl | phenyl | phenyl | n-Propyl |
| (263) | n-Pentyl | phenyl | phenyl | n-Pentyl |
| (264) | n-Butoxy | phenyl | phenyl | n-Propyl |
| (265) | n-Butoxy | phenyl | phenyl | n-Pentyl |
| (266) | n-Pentyl | pyrazine | phenyl | Methyl |
| (267) | n-Pentyl | pyrazine | phenyl | Ethyl |
| (268) | n-Pentyl | pyrazine | phenyl | n-Propyl |
| (269) | n-Butoxy | pyrazine | phenyl | n-Heptyl |
| (270) | n-Pentyl | pyridine | phenyl | Methyl |
| (271) | n-Pentyl | pyridine | phenyl | Ethyl |
| (272) | n-Pentyl | pyridine | phenyl | n-Propyl |
| (273) | n-Pentyl | pyridine | phenyl | n-Pentyl |
| (274) | n-Propyl | — | —C₂H₄—biphenyl— | Ethyl |

-continued

| | R | $(A^1-Z^1)_m$ | $(Z^2-A^2)_m$ | X |
|---|---|---|---|---|
| (275) | n-Propyl | — | —C₂H₄—⬡—⬡— | n-Propyl |
| (276) | n-Propyl | — | —C₂H₄—⬡—⬡— | n-Butyl |
| (277) | n-Propyl | — | —C₂H₄—⬡—⬡— | n-Pentyl |
| (278) | n-Propyl | —⬡(F,F)— | —⬡— | Ethyl |
| (279) | n-Propyl | —⬡(H)— | —⬡(F)— | n-Propyl |
| (280) | n-Propyl | —⬡(H)— | —⬡— | Methyl |
| (281) | n-Propyl | —⬡(H)— | —⬡— | Ethyl |
| (282) | n-Propyl | —⬡(H)— | —⬡— | n-Propyl, C 57 N 96 I |
| (283) | n-Propyl | —⬡(H)— | —⬡— | n-Pentyl |
| (284) | Ethoxy | —⬡—C₂H₄— | —⬡— | n-Propyl |
| (285) | Ethoxy | —⬡—C₂H₄— | —⬡— | n-Pentyl |
| (286) | n-Propyl | — | —⬡—⬡(F)— | n-Propyl |

| R | $(A^1-Z^1)_m$ | $(Z^2-A^2)_m$ | X |
|---|---|---|---|
| (287) n-Propyl | — | [2-fluoro-biphenyl] | n-Propyl |
| (288) n-Propyl | — | [pyrimidine-phenyl] | n-Propyl |
| (289) n-Propyl | — | [pyrimidine-phenyl] | n-Pentyl |
| (290) n-Propyl | — | [pyrimidine-phenyl] | n-Heptyl |
| (291) n-Pentyl | [cyclohexyl H] | [phenyl-cyclohexyl H] | n-Propyl, C 97 N 270 I |

EXAMPLE 292

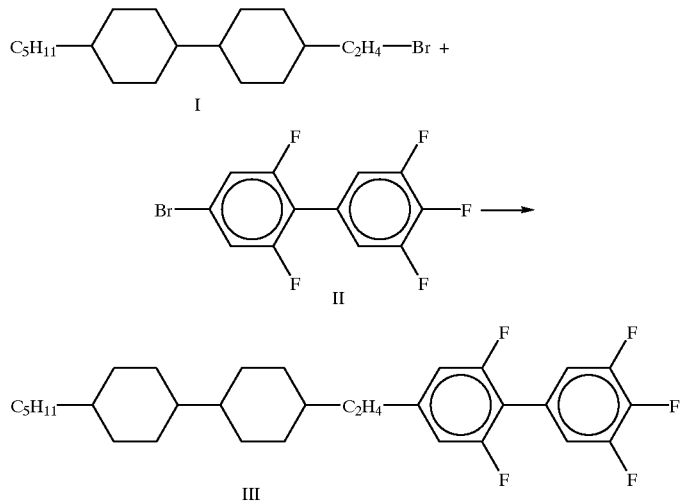

0.1 mol of I are introduced into 150 ml of a solvent mixture of THF/toluene (1:4 ratio by volume), and 11.5 g of anhydrous zinc bromide and then 1.4 g of lithium granules are then added. The mixture is treated with ultrasound for 4 hours at between 0° C. and 10° C. under argon and with stirring in order to convert I into the corresponding dialkyl zinc compound. The organozinc compound is treated with 0.1 mol of II and 1.5 g (2 mol%) of 1,1'-bis (diphenylphosphino)ferrocene/palladium(II) dichloride ($PdCl_2$ dppf), and the mixture is stirred at room temperature for 24 hours after the ultrasound bath and the cooling have been removed. The mixture is decomposed using 100 ml of saturated $NH_4Cl$ solution with stirring, the organic phase is separated off, and the aqueous phase is extracted 2× with toluene. The combined organic extracts are dried, evaporated and chromatographed on silica gel using hexane to give III.

EXAMPLE 293

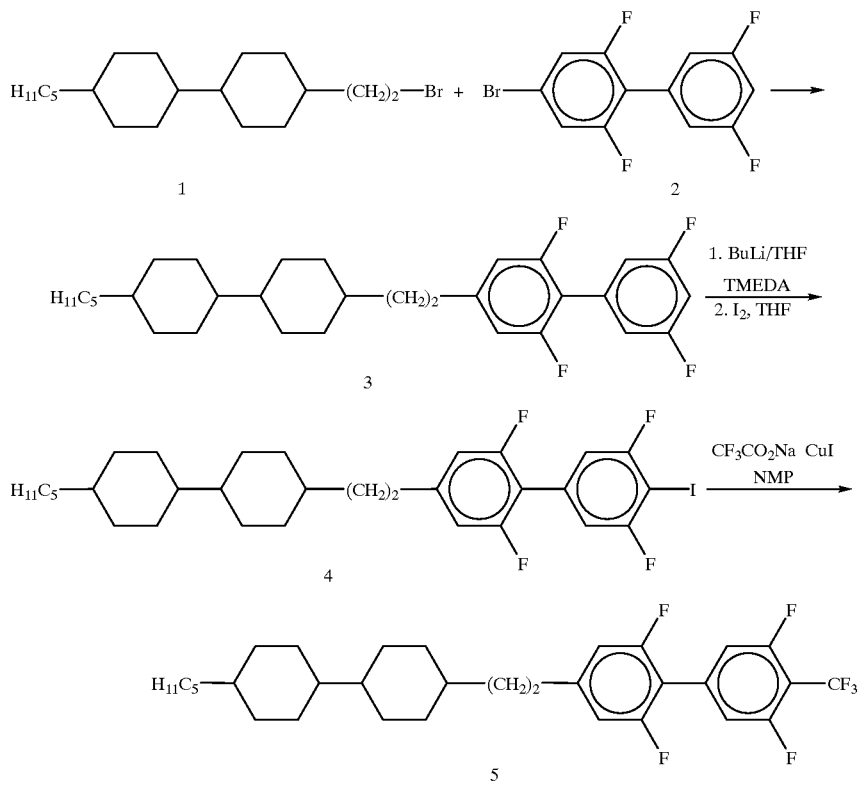

100 mmol of 1 are converted into 3 by reaction with 2 analogously to the above example.

31 ml of n-BuLi (15% in hexane) are added dropwise at −65 to −70° C. to a mixture of 47 mmol of 3, 7.5 ml of TMEDA (50 mmol) and 150 ml of THF, and the mixture is stirred for a further 1 hour at −70° C. A solution of 12.0 g (47 mmol) of iodine in 25 ml of THF is then added dropwise at −65 to −70° C., and the mixture is stirred for a further 0.5 hour at −70° C. The mixture is warmed to −30° C and hydrolyzed during 15 ml of water, and excess iodine is reduced by adding 15 ml of sodium bisulfite solution. Customary work-up and recrystallization from hexane give 4. 400 ml of NMP are removed by distillation from a mixture of 38 mmol of 4, 4.4 g (76 mmol) of KF, 22.8 g (168 mmol) of sodium trifluoroacetate and 800 ml of NMP at 70° C. and 4 mbar. 1.4 g (76 mmol) of dried CuI are then added to the reaction mixture, which is stirred at 160° C. for 5 hours. About 300 ml of NMP are subsequently removed by distillation. The mixture is allowed to cool to RT, and 400 ml of MTB ether are added. The mixture is washed with water, dried using $Na_2SO_4$, filtered and evaporated to give a residue. Chromatography on silica gel using hexane gives 5.

EXAMPLE 294

A solution of 0.1 m of 1-(trans-4-n-propylcyclohexyl)-2-(3,3',5'-trifluorobiphenylyl)ethane and 0.1 m of TMEDA in 300 ml of THF is treated dropwise at about −65° with 0.1 m of n-BuLi (1.5 M in hexane). The mixture is stirred at this temperature for a further 30 minutes, and 0.2 m of N-chlorosuccinimide in 70 ml of THF is then slowly added. When the addition is complete, the mixture is allowed to warm to −20° and is hydrolyzed using $H_2O$. The product is dissolved completely by adding diethyl ether. Extractive work-up and purification by chromatography and crystallization give 1-(trans-4-n-propylcyclohexyl)-2-(4'-chloro-3, 3',5'-trifluorobiphenylyl)ethane.

EXAMPLE 301

A mixture of 10.5 g of 1-bromo-3,4-difluorobenzene, 17.4 g of 4-(trans-4-4-propylcyclohexyl)-2,6-difluorostyrene (obtainable in accordance with the abovementioned schemes), 0.25 g of Pd acetate, 0.6 g of tri-o-tolylphosphine, 7 g of triethylamine and 125 ml of acetonitrile is refluxed until the reaction is complete. Customary work-up gives trans-1-(3,4-difluorophenyl)-2-[4-(trans-4-propylcyclohexyl)-2,6-difluorophenyl]ethene, C 101 N 156.5 I.

The following are prepared analogously: trans-1-(3,4-difluorophenyl)-2-(2,6-difluoro-4-ethoxyphenyl)ethene, C 92 I.

EXAMPLE A

A liquid-crystalline medium I comprises

| | |
|---|---|
| PCH-5F | 10.0% |
| PCH-6F | 8.0% |
| PCH-7F | 6.0% |
| CCP-20CF3 | 8.0% |
| CCP-30CF3 | 12.0% |
| CCP-40CF3 | 9.0% |
| CCP-50CF3 | 9.0% |
| BCH-3F.F | 12.0% |
| BCH-5F.F | 10.0% |
| ECCP-30CF3 | 5.0% |
| ECCP-50CF3 | 5.0% |
| CBC-33F | 2.0% |

-continued

| | |
|---|---|
| CBC-53F | 2.0% |
| CBC-55F | 2.0% |

A medium II according to the invention comprises 90% of medium I and 10% of

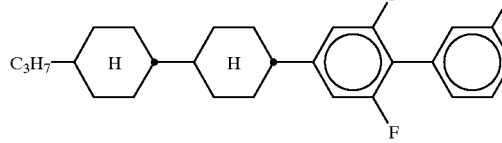

| | Medium I | Medium II |
|---|---|---|
| Clear point | 91° C. | 102.4° C. |
| Δn | 0.094 | 0.102 |
| Δε | 5.2 | 6.0 |
| Viscosity at 20° (cSt) | 15.0 | 16.7 |

What is claimed is:

1. A 1,4-disubstituted 2,6-difluorobenzene compound of formula I

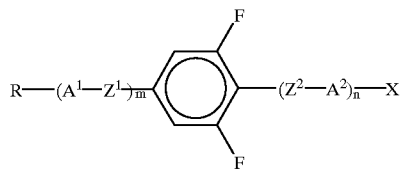

wherein

R is an alkyl radical having 1 to 15 carbon atoms which is unsubstituted or at least monosubstituted by halogen, it also being possible for one or more $CH_2$ groups in these radicals to be replaced, in each case independently of one another, by —O—, —S—,

—CO—, —CO—O—, —O—CO— or —O—CO—O— in such a manner that oxygen atoms are not linked directly to one another, $A^1$ and $A^2$, in each case independently of one another, are (a) a 1,4-phenylene radical in which in addition, one or two CH groups may be replaced by N, or (b) a radical from the group comprising 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by CN or monosubstituted or disubstituted by fluorine, $Z^1$ and $Z^2$ in each case independently of one another, are —CO—O—, —O—CO—, —$CH_2$O—, —O$CH_2$—, —$CH_2CH_2$—, —CH=CH—, —C≡C— or a single bond m is 0, 1, or 2 and n is 1 or 2, where (m+n) is 1, 2 or 3, and X is F, Cl, —$OCF_3$, or —$OCHF_2$, with the proviso that at least one of the radicals $A^1$ and $A^2$ present in the molecule is

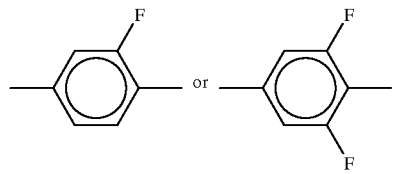

2. A liquid-crystalline medium according to claim 1 containing at least two liquid-crystalline components, wherein at least one compound is one of formula I.

3. A liquid-crystal display element, comprising a liquid-crystalline medium according to claim 2.

4. An electrooptical display element, comprising as a dielectric, a liquid-crystalline medium according to claim 2.

* * * * *

UNITED STATES PATENT AND TRADEMARK OFFICE
CERTIFICATE OF CORRECTION

PATENT NO. : 6,200,654 B1
DATED : March 13, 2001
INVENTOR(S) : Eike Poetsch et al.

It is certified that error appears in the above-identified patent and that said Letters Patent is hereby corrected as shown below:

Column 1,
Lines 5-10 should read as follows:

-- This is a continuation of application Serial No. 08/449,559, filed May 24, 1995, which is a divisional of application Serial No. 08/402,555, filed March 13, 1995, which is a continuation of Serial No. 07/659,320, filed February 22, 1991, now abandoned, which is a 371 of PCT/EP90/02109 of December 6, 1990. --

Signed and Sealed this

Seventh Day of May, 2002

Attest:

Attesting Officer

JAMES E. ROGAN
Director of the United States Patent and Trademark Office